United States Patent
Kaita

(10) Patent No.: US 11,408,843 B2
(45) Date of Patent: Aug. 9, 2022

(54) GAS SENSOR

(71) Applicant: TDK Corporation, Tokyo (JP)

(72) Inventor: Yoshio Kaita, Tokyo (JP)

(73) Assignee: TDK CORPORATION, Tokyo (JP)

( * ) Notice: Subject to any disclaimer, the term of this patent is extended or adjusted under 35 U.S.C. 154(b) by 514 days.

(21) Appl. No.: 16/479,338

(22) PCT Filed: Nov. 9, 2017

(86) PCT No.: PCT/JP2017/040349
§ 371 (c)(1),
(2) Date: Jul. 19, 2019

(87) PCT Pub. No.: WO2018/135100
PCT Pub. Date: Jul. 26, 2018

(65) Prior Publication Data
US 2019/0353607 A1    Nov. 21, 2019

(30) Foreign Application Priority Data
Jan. 19, 2017  (JP) ................................ 2017-007319

(51) Int. Cl.
*G01N 27/18* (2006.01)
*G01N 27/16* (2006.01)
(Continued)

(52) U.S. Cl.
CPC .......... *G01N 27/18* (2013.01); *G01N 27/028* (2013.01); *G01N 27/16* (2013.01); *G01N 33/004* (2013.01); *G01N 33/0031* (2013.01)

(58) Field of Classification Search
CPC ........ G01N 27/04; G01N 27/14; G01N 27/18; G01N 27/028; G01N 27/16; G01N 33/0031; G01N 33/004
See application file for complete search history.

(56) References Cited

U.S. PATENT DOCUMENTS

| | | | |
|---|---|---|---|
| 2009/0193872 A1* | 8/2009 | Tokuda | G01N 27/18 73/23.31 |
| 2012/0047995 A1 | 3/2012 | Fleischer et al. | |
| 2015/0100167 A1* | 4/2015 | Sloo | H04L 67/24 700/278 |

FOREIGN PATENT DOCUMENTS

| | | | |
|---|---|---|---|
| EP | 0849588 A2 * | 6/1998 | F01N 11/00 |
| JP | 07-260730 A | 10/1995 | |

(Continued)

OTHER PUBLICATIONS

International Search Report issued in corresponding International Patent Application No. PCT/JP2017/040349, dated Dec. 26, 2017, with English Translation.

*Primary Examiner* — Benjamin R Schmitt

(74) *Attorney, Agent, or Firm* — McDermott Will & Emery LLP

(57) ABSTRACT

A gas sensor includes a first sensor part that can detect the concentration of the mixture of a first gas and a second gas, a second sensor part having higher detection sensitivity with respect to the second gas than with respect to the first gas, and a signal processing circuit that subtracts the concentration of the second gas detected by the second sensor part from the mixture concentration detected by the first sensor part to derive the concentration of the first gas. The concentration of the second gas detected by the second sensor part is subtracted from the concentration of the mixture concentration detected by the first sensor part, so that it is possible to cancel the influence of the second gas which is miscellaneous gas to thereby work out a correct value of concentration of the first gas to be detected.

12 Claims, 17 Drawing Sheets

(51) Int. Cl.
*G01N 33/00* (2006.01)
*G01N 27/02* (2006.01)

(56) References Cited

FOREIGN PATENT DOCUMENTS

| JP | 2001-175969 A | 6/2001 |
| JP | 2002-323468 A | 11/2002 |

\* cited by examiner

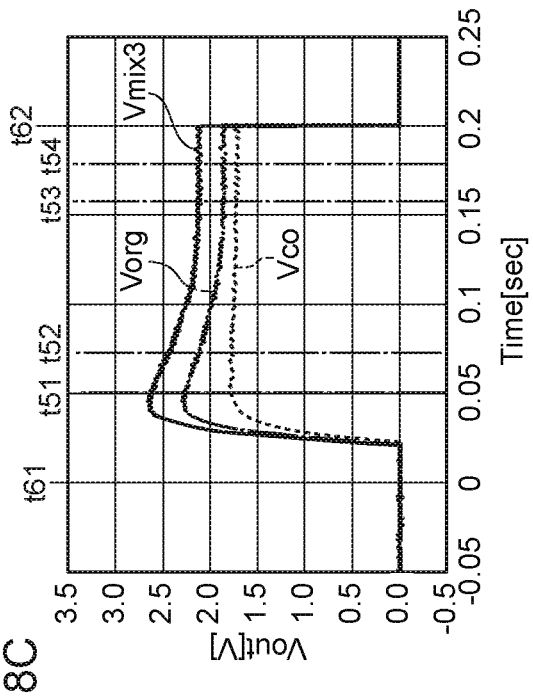
FIG. 8C
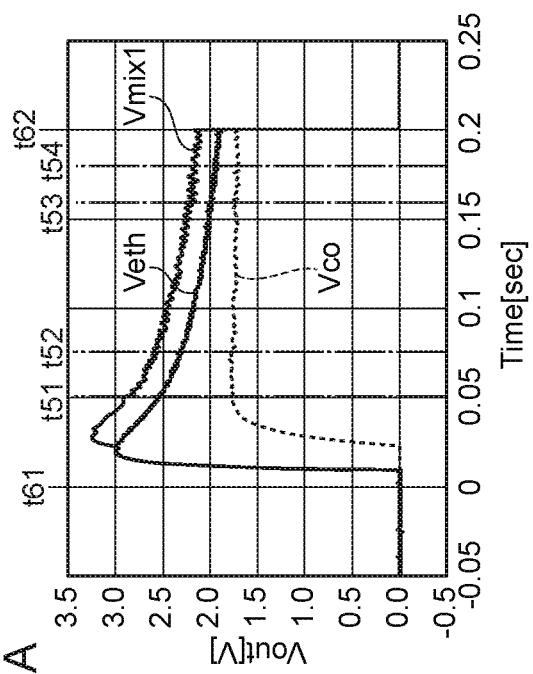
FIG. 8A
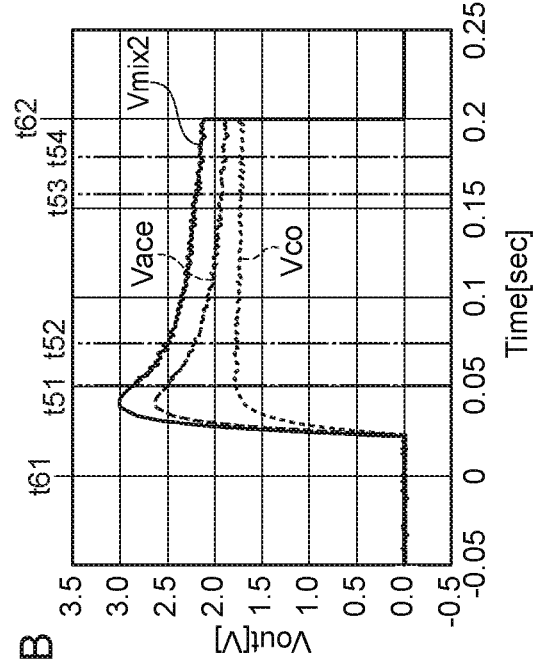
FIG. 8B
FIG. 8D
| | (C1-C2)/(C3-C4) Inclination Ratio | |
|---|---|---|
| | Without CO | With CO |
| Ethanol | 3 | 5.5 |
| Organic Deodorant | 8 | 20 |
| Acetic Acid | 8 | 20 |

GAS SENSOR

CROSS REFERENCE

This application is the U.S. National Phase under 35 U.S.C. § 371 of International Application No. PCT/JP2017/040349, filed on Nov. 9, 2017, which claims the benefit of Japanese Application No. 2017-007319, filed on Jan. 19, 2017, the entire contents of each are hereby incorporated by reference.

TECHNICAL FIELD

The present invention relates to a gas sensor for detecting gas contained in the atmosphere and, more particularly, to a gas sensor capable of canceling the influence of miscellaneous gas different from detection target gas.

BACKGROUND ART

In recent years, gas sensors capable of detecting gases harmful to a human body have been prevailing. For example, Patent Documents 1 and 2 propose a contact combustion type gas sensor capable of discriminating between a detection target gas and miscellaneous gas which is non-detection target gas.

CITATION LIST

Patent Document

[Patent Document 1] JP 2001-175969 A
[Patent Document 2] JP 2002-323468 A

SUMMARY OF INVENTION

Problem to be Solved by the Invention

However, although the gas sensors described in Patent Documents 1 and 2 are capable of discriminating between a detection target gas and a non-detection target gas, they can hardly accurately measure the concentration of the detection target gas when the detection target gas and miscellaneous gas coexist.

It is therefore an object of the present invention to provide a gas sensor capable of accurately measuring the concentration of detection target gas when the detection target gas and miscellaneous gas coexist.

Means for Solving the Problem

A gas sensor according to the present invention includes a first sensor part that can detect the concentration of the mixture of first gas and second gas, a second sensor part having higher detection sensitivity with respect to the second gas than with respect to the first gas, and a signal processing circuit that subtracts the concentration of the second gas detected by the second sensor part from the mixture concentration detected by the first sensor part to derive the concentration of the first gas.

According to the present invention, the concentration of the second gas detected by the second sensor part is subtracted from the concentration of the mixture concentration detected by the first sensor part, so that it is possible to cancel the influence of the second gas which is miscellaneous gas to thereby work out a correct value of concentration of the first gas to be detected.

In the present invention, it is preferable that the first and second gases are combustible gas and that the first sensor part is a contact combustion type sensor, and it is more preferable that the first gas is closer in heat conductivity to the measuring environmental atmosphere than the second gas is and that the second sensor part is a heat conduction type sensor. With this configuration, it is possible to reduce measurement error caused due to the presence of combustible miscellaneous gas. The first gas is, e.g., CO gas, and the second gas is, e.g., ethanol, acetic acid, or an organic deodorant.

In the present invention, it is preferable that the first sensor part includes a first thermistor and a catalyst disposed near the first thermistor and that the second sensor part includes a second thermistor and does not include a catalyst near the second thermistor. With this configuration, it is possible to accelerate combustion of gas to be detected.

In this case, the second sensor part may further include a resistor, the second thermistor may be shared between the first and second sensor parts, the first sensor part may output a first detection signal from the connection point between the first and second thermistors, and the second sensor part may output a second detection signal from the connection point between the second thermistor and the resistor. With this configuration, the number of required elements can be reduced. In this case, the second sensor part preferably further includes a dummy catalyst disposed near the second thermistor and having no catalytic function. With this configuration, it is possible to reduce measurement error due to aging of the thermistor, a change in environmental temperature, or the presence of non-combustible miscellaneous gas.

Alternatively, the gas sensor may have a configuration in which the first sensor part includes first and second thermistors and a catalyst disposed near the first thermistor, the second sensor part includes a third thermistor and a resistor, the first sensor part outputs a first detection signal from the connection point between the first and second thermistors, the second sensor part outputs a second detection signal from the connection point between the third thermistor and the resistor, and a catalyst is not disposed near the second thermistor. With this configuration, measurement by the first sensor part and measurement by the second sensor part can be executed synchronously (at the same time) or asynchronously (at different times). In this case, the first sensor part preferably further includes a dummy catalyst disposed near the second thermistor and having no catalytic function. With this configuration, it is possible to reduce measurement error due to aging of the thermistor, a change in environmental temperature, or presence of non-combustible miscellaneous gas. Further, the second sensor part may include a fourth thermistor connected in parallel to the resistor. This allows measurement error due to humidity to be canceled. Further, the concentration of $CO_2$ gas can be measured using the second sensor part.

In the present invention, the signal processing circuit preferably determines the type of the second gas based on the first detection signal. This allows the cancel operation to be performed more accurately according to the type of the miscellaneous gas. In this case, the signal processing circuit can determine the type of the second gas from the rising waveform of the first detection signal. Further, the signal processing circuit may determine the presence/absence of the first gas according to the inclination of the first detection signal.

In the present invention, the signal processing circuit may calculate the concentration of the first gas in a predetermined detection cycle, and the detection cycle may be reduced when the concentration of the second gas detected by the second sensor part exceeds a predetermined value. This allows miscellaneous gas adhering to the first sensor part to be removed immediately.

In the present invention, the signal processing circuit preferably corrects the difference between detection sensitivity with respect to the second gas by the first sensor part and detection sensitivity with respect to the second gas by the second sensor part. Thus, it is possible to accurately cancel the influence of miscellaneous gas by the sensitivity correction.

Advantageous Effect of the Invention

As described above, according to the present invention, it is possible to accurately measure the concentration of detection target gas when the detection target gas and miscellaneous gas coexist.

BRIEF DESCRIPTION OF DRAWINGS

FIG. 5A illustrates output waveforms of the first sensor part S1, FIG. 5B illustrates output waveforms of the second sensor part S2, and FIG. 5C shows a calculation result of the differential value.

FIGS. 8A to 8C are views illustrating the waveforms of signals output from the differential amplifier 21 when various types of gas exist in the measuring environmental atmosphere in the measurement using the first sensor part S1, where FIG. 8A illustrates a case where CO gas, ethanol, or a mixture thereof exists, FIG. 8B illustrates a case where CO gas, acetic acid, or a mixture thereof exists, FIG. 8C illustrates a case where CO gas, organic deodorant, or a mixture thereof exists. FIG. 8D is a table showing, for each type of miscellaneous gas, the ratio of inclination between waveforms obtained when CO gas is present and when not present.

MODE FOR CARRYING OUT THE INVENTION

Preferred embodiments of the present invention will be explained below in detail with reference to the accompanying drawings.

First Embodiment

Figure 1:
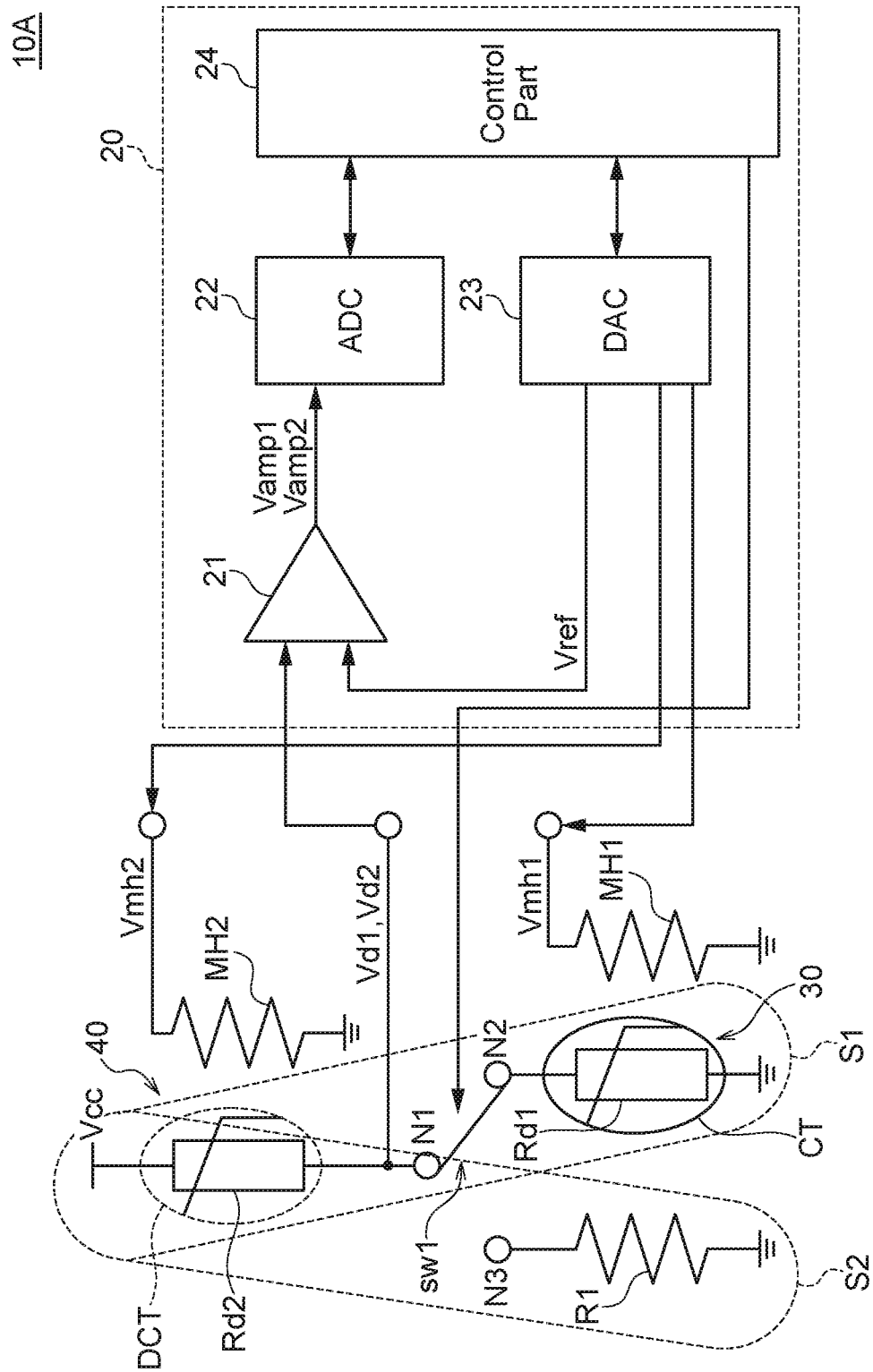
FIG. 1 is a circuit diagram illustrating the configuration of a gas sensor 10A according to a first embodiment of the present invention.

FIG. 1 is a circuit diagram illustrating the configuration of a gas sensor 10A according to the first embodiment of the present invention.

As illustrated in FIG. 1, the gas sensor 10A according to the present embodiment includes a first sensor part S1, a second sensor part S2, and a signal processing circuit 20. Although not particularly limited, the gas sensor 10A according to the present embodiment is configured to detect the concentration of CO gas in the atmosphere and is capable of cancelling the influence of miscellaneous gas such as ethanol, acetic acid, or an organic deodorant, as will be described later.

The first sensor part S1 is a contact combustion type gas sensor for detecting the concentration of CO gas to be detected and has a configuration in which a first thermistor Rd1 and a second thermistor Rd2 are connected in series between power supply lines (Vcc and GND lines). The first and second thermistors Rd1 and Rd2 are each made of a material having a negative resistance-temperature coefficient, such as a composite metal oxide, amorphous silicon, polysilicon, or germanium. The first thermistor Rd1 is covered with a catalyst CT, and the second thermistor Rd2 is covered with a dummy catalyst DCT.

The catalyst CT may be obtained by making platinum (Pt)-carrying γ alumina into a paste form together with a binder, followed by coating/sintering. The material to be carried on the γ alumina may be catalytic metal such as gold (Au) or palladium (Pd). On the other hand, the dummy catalyst DCT is made of γ alumina not containing a catalytic metal such as platinum (Pt) and is provided for matching the heat capacity of the first thermistor Rd1 and that of the second thermistor Rd2.

When being heated to a predetermined temperature by a first heater resistor MH1, the catalyst CT accelerates a reaction (combustion) between CO gas to be detected and $O_2$ gas in the atmosphere to generate $CO_2$ gas. Reaction heat generated at this time is conducted to the first thermistor Rd1 to change the resistance value thereof. On the other hand, the dummy catalyst DCT does not accelerate combustion of CO gas even when being heated to a predetermined temperature by a second heater resistor MH2, so that the resistance value of the second thermistor Rd2 reflects only heating by the second heater resistor MH2.

Thus, a first detection signal Vd1 output from the connection point between the first and second thermistors Rd1 and Rd2 has a level corresponding to the concentration of combustible gas in the measuring environmental atmosphere. The first detection signal Vd1 is input to the signal processing circuit 20

The second sensor part S2 is a heat conduction type gas sensor for detecting the concentration of miscellaneous gas such as ethanol, acetic acid, or organic deodorant and has a configuration in which the second thermistor Rd2 and a resistor R1 are connected in series between the power supply lines (Vcc and GND lines). As illustrated in FIG. 1, the second thermistor Rd2 is shared between the first and second sensor parts S1 and S2, and switching thereof between the first and second sensor parts S1 and S2 is made by a switch SW1.

A second detection signal Vd2 is taken from the connection point between the second thermistor Rd2 and the resistor R1 and is input to the signal processing circuit 20.

The signal processing circuit 20 includes a differential amplifier 21, an AD converter (ADC) 22, a DA converter (DAC) 23, and a control part 24. The differential amplifier 21 compares the first or second detection signal Vd1 or Vd2 and a reference voltage Vref and amplifies the difference therebetween. Amplification signals Vamp1 and Vamp2 output from the differential amplifier 21 are input to the AD converter 22. The AD converter 22 performs digital conversion of the amplification signals Vamp1 and Vamp2 and supplies the values thereof to the control part 24. On the other hand, the DA converter 23 performs analog conversion of a reference signal supplied from the control part 24 to generate the reference voltage Vref and to generate control voltages Vmh1 and Vmh2 to be supplied respectively to the first and second heater resistors MH1 and MH2. Further, the control part 24 controls various operations to be described later, such as switching of the switch SW1.

Figure 2:
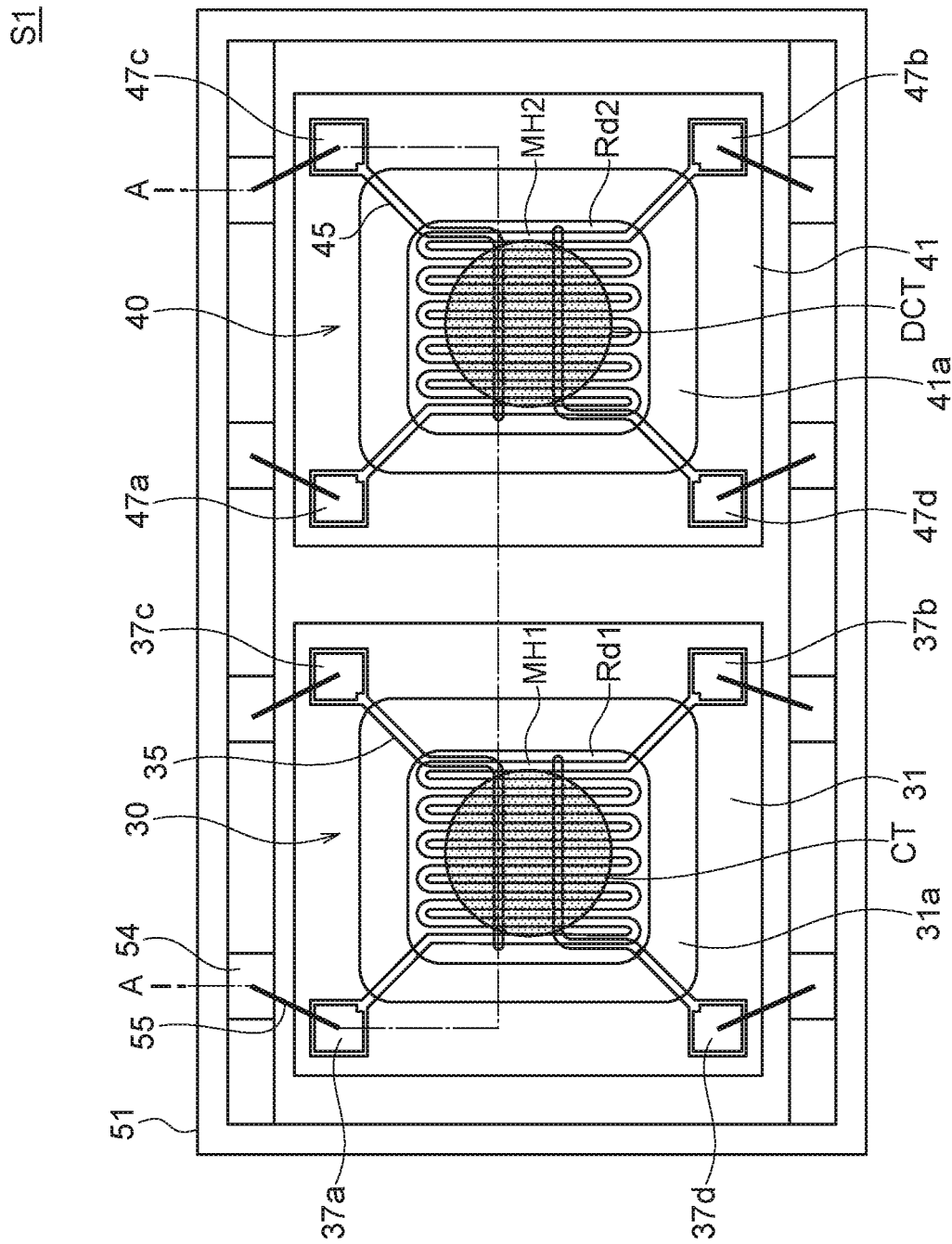
FIG. 2 is a top view for explaining the configuration of the first sensor part S1.
Figure 3:
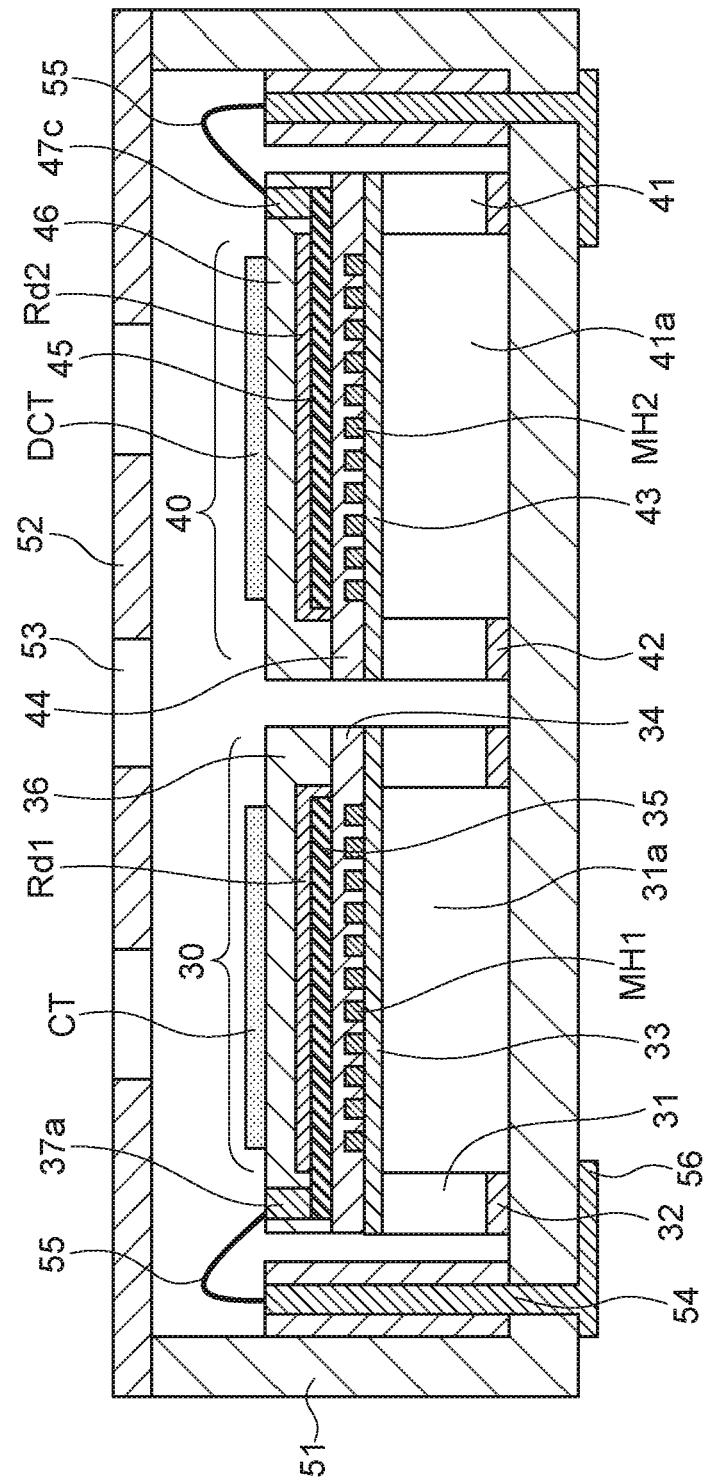
FIG. 3 is a cross-sectional view taken along line A-A in FIG. 2.

FIG. 2 is a top view for explaining the configuration of the first sensor part S1. FIG. 3 is a cross-view taken along line A-A in FIG. 2. It should be noted that the drawing is a schematic diagram, and the relationship between the thickness and the planar size, the thickness ratio between the devices, and the like may differ from those in the actual structure for descriptive convenience within a range where the effects of the present embodiment can be obtained.

The first sensor part S1 is a contact combustion type gas sensor for detecting gas concentration based on a catalytic reaction of combustible gas and includes, as illustrated in FIGS. 2 and 3, two detection parts 30 and 40 and a ceramic package 51 for housing the detection parts 30 and 40. As described above, although combustible gas to be detected is CO gas, miscellaneous combustible gas which is a non-detection target gas, such as ethanol, acetic acid, or an organic deodorant, is detected inevitably.

The ceramic package 51 is a box-shaped case having an opened upper part, and a lid 52 is provided at the upper part. The lid 52 has a plurality of vent holes 53, through which combustible gas in the atmosphere can flow into the ceramic package 51. In FIG. 2, the lid 52 is omitted for ease of viewing.

The detection part 30 includes insulating films 32 and 33 formed respectively on the lower and upper surfaces of a substrate 31, a first heater resistor MH1 provided on the insulating film 33, a heater protective film 34 covering the first heater resistor MH1, a first thermistor Rd1 and a thermistor electrode 35 which are provided on the heater protective film 34, a thermistor protective film 36 covering the first thermistor Rd1 and thermistor electrode 35, and a catalyst CT provided on the thermistor protective film 36.

There is no particular restriction on the material of the substrate 31 as long as it has an adequate mechanical strength and is suitable for fine processing such as etching, and, examples thereof include a silicon single crystal substrate, a sapphire single crystal substrate, a ceramic substrate, a quartz substrate, a glass substrate, and the like. A cavity 31a is provided at a position overlapping the first heater resistor MH1 in a plan view so as to suppress conduction of heat due to the first heater resistor MH1 to the substrate 31. A part where the substrate 31 is removed by the cavity 31a is called a membrane. The presence of the membrane reduces heat capacity by the thinning of the substrate 31, allowing heating to be achieved with less power consumption.

The insulating films 32 and 33 are each made of an insulating material such as silicon oxide or silicon nitride. When silicon oxide is used as the insulating films 32 and 33, a film deposition method such as a thermal oxidation method or a CVD (Chemical Vapor Deposition) method may be used. There is no particular restriction on the thickness of the insulating films 32 and 33 as long as the insulating property thereof is ensured and may be, e.g., about 0.1 μm to 1.0 μm. Particularly, the insulating film 33 is used also as an etching stop layer when the cavity 31a is formed in the substrate 31, so that the thickness thereof is preferably set to a value suitable for fulfilling the function as the etching stop layer.

The first heater resistor MH1 is made of a conductive substance whose resistivity changes depending on temperature and is preferably made of a metal material having a comparatively high melting point, such as molybdenum (Mo), platinum (Pt), gold (Au), tungsten (W), tantalum (Ta), palladium (Pd), iridium (Ir), or an alloy containing two or more of them. Among them, a conductive material that can be subjected to high accuracy dry etching such as ion milling is preferable, and more preferably, it contains platinum (Pt) having high corrosion resistance as a main component. Further, an adhesion layer such as a titanium (Ti) layer is preferably formed as a base of Pt so as to improve adhesion with respect to the insulating film 33.

The heater protective film 34 is formed above the first heater resistor MH1. The heater protective film 34 is preferably made of the same material as the insulating film 33. The first heater resistor MH1 generates violent thermal changes (repetition of temperature rises between several ten degrees to several hundred degrees and then a drop to room temperature), so that strong thermal stress is applied to the insulating film 33 and heater protective film 34. When being continuously subject to the thermal stress, the insulating film 33 and heater protective film 34 may suffer damage such as interlayer peeling or crack. However, when the insulating film 33 and the heater protective film 34 are made of the same material, material characteristics thereof are the same, and adhesion strength therebetween is high, so that the damage such as interlayer peeling or crack is less likely to occur as compared to when the insulating film 33 and the heater protective film 34 are made of mutually different materials. When silicon oxide is used as the material of the heater protective film 34, film deposition may be performed by a thermal oxidation method or a CVD method. The film thickness of the heater protective film 34 is not particularly restricted as long as insulation between the first thermistor Rd1 and the thermistor electrode 35 can be ensured and may be, e.g., 0.1 μm to 3.0 μm.

The first thermistor Rd1 is made of a material having a negative resistance-temperature coefficient, such as a composite metal oxide, amorphous silicon, polysilicon, or germanium and can be formed by using a thin-film process such as a sputtering method or a CVD method. The film thickness of the first thermistor Rd1 may be adjusted according to a target resistance value. For example, when the resistance value (R25) at room temperature is set to about 2 MΩ using MnNiCo based oxide, the film thickness may be set to about 0.2 μm to 1 μm although it depends on the distance between a pair of thermistor electrodes 35. The reason that the thermistor is used as a temperature-sensitive resistive element is that the thermistor is larger in resistance temperature coefficient than a platinum temperature detector and can thus obtain high detection sensitivity. Further, heat generation of the first heater resistor MH1 and catalyst CT can efficiently be detected because of the thin-film structure.

The thermistor electrode 35 is configured of a pair of electrodes arranged spaced apart from each other at a predetermined interval, and the first thermistor Rd1 is provided between the pair of thermistor electrodes 35. With this configuration, the resistance value between the pair of thermistor electrodes 35 is determined by the resistance value of the first thermistor Rd1. The thermistor electrode 35 may be made of a conductive substance that can endure a process such as a film deposition step and a heat treatment process for the first thermistor Rd1 and is preferably made of a material having a comparatively high melting point, such as molybdenum (Mo), platinum (Pt), gold (Au), tungsten (W), tantalum (Ta), palladium (Pd), iridium (Ir), or an alloy containing two or more of them.

The first thermistor Rd1 and thermistor electrode 35 are covered with the thermistor protective film 36. When the first thermistor Rd1 is brought into contact with a material having reducibility so as to make it turn into a high-temperature state, the material deprives the thermistor of oxygen to cause a reduction, thus affecting thermistor characteristics. To prevent this, an insulating oxide film having no reducibility, such as silicon oxide film, is preferably used as the material of the thermistor protective film 36.

As illustrated in FIG. 2, both ends of the first heater resistor MH1 are connected respectively to electrode pads 37a and 37b provided on the surface of the thermistor protective film 36. Further, both ends of the thermistor electrode 35 are connected respectively to electrode pads 37c and 37d provided on the surface of the thermistor protective film 36. The electrode pads 37a to 37d are connected to a package electrode 54 installed to the ceramic package 51 through a bonding wire 55. The package electrode 54 is connected to the signal processing circuit 20 illustrated in FIG. 1 through an external terminal 56 provided on the back surface of the ceramic package 51.

The catalyst CT is obtained by carrying a catalytic metal such as platinum (Pt) on γ alumina. When being heated to a predetermined temperature by the first heater resistor MH1, the catalyst CT accelerates a reaction (combustion) between a combustible gas and $O_2$ gas in the atmosphere. For example, when CO gas which is a detection target exists, the catalyst CT accelerates a reaction (combustion) between CO gas and $O_2$ gas in the atmosphere to generate $CO_2$ gas. Reaction heat generated at this time is conducted to the first thermistor Rd1 to change the resistance value thereof.

As described above, the detection part 30 has a configuration in which the first heater resistor MH1, first thermistor Rd1, and catalyst CT are laminated on the substrate 31, so that heat generated by the first heater resistor MH1 is efficiently conducted to the catalyst CT and first thermistor Rd1, and reaction heat of the catalyst CT is efficiently conducted to the first thermistor Rd1.

On the other hand, the detection part 40 includes insulating films 42 and 43 formed respectively on the lower and upper surfaces of a substrate 41, a second heater resistor MH2 provided on the insulating film 43, a heater protective film 44 covering the second heater resistor MH2, a second thermistor Rd2 and a thermistor electrode 45 which are provided on the heater protective film 44, a thermistor protective film 46 covering the second thermistor Rd2 and thermistor electrode 45, and a dummy catalyst DCT provided on the thermistor protective film 46.

The substrate 41 is made of the same material as the substrate 31 used for the detection part 30 and has the same configuration as the substrate 31. That is, a cavity 41a is provided at a position overlapping the second heater resistor MH2 in a plan view so as to suppress heat due to the second heater resistor MH2 from conducting to the substrate 41. The insulating films 42 and 43 are made of the same material (insulating material such as silicon oxide or silicon nitride) as the insulating films 32 and 33. The insulating films 42 and 43 have the same thickness as the insulating films 32 and 33.

The second heater resistor MH2, heater protective film 44, second thermistor Rd2, thermistor electrode 45, and thermistor protective film 46 have the same configurations as the first heater resistor MH1, the heater protective film 34, the first thermistor Rd1, the thermistor electrode 35, and the thermistor protective film 36, respectively, used for the detection part 30. Both ends of the second heater resistor MH2 are connected respectively to electrode pads 47a and 47b provided on the surface of the thermistor protective film 46.

Further, the both ends of the thermistor electrode 45 are connected respectively to electrode pads 47c and 47d provided on the surface of the thermistor protective film 46. The electrode pads 47a to 47d are connected to the package electrode 54 fitted in the ceramic package 51 through the bonding wire 55.

The dummy catalyst DCT has the same configuration as the catalyst CT except that it does not contain a catalytic metal such as platinum (Pt). Thus, the dummy catalyst DCT has no catalytic function and is provided only for matching the heat capacity of the detection part 30 and that of the detection part 40.

The thus configured detection parts 30 and 40 are each produced in multiple numbers in a wafer state at a time, followed by dicing into individual pieces, and then fixed to the ceramic package 51 using a die paste (not illustrated). Thereafter, electrode pads 37a to 37d and 47a to 47d are connected to their corresponding package electrodes 54 through the bonding wires 55 using a wire bonding machine. As the material of the bonding wire 55, a metal having low resistance, such as Au, Al, or Cu is preferably used.

Finally, adhesive resin (not illustrated) or the like is used to fix the lid 52 having the outside air vent holes 53 to the ceramic package 51. Although a substance contained in the adhesive resin is turned into gas during heating/curing of the adhesive resin (not shown), the gas is easily discharged outside the package through the vent holes 53, so that the detection parts 30 and 40 are hardly affected.

The thus accomplished first sensor part S1 is connected to the signal processing circuit 20 or a power supply through the external terminal 56. The switch SW1 and the resistor R1 constituting the second sensor part S2 are incorporated in the signal processing circuit 20 or provided on a circuit board on which the signal processing circuit 20 is mounted.

The configuration of the gas sensor 10A according to the present embodiment has been described. Next, the operation of the gas sensor 10A according to the present embodiment will be described.

Figure 4:
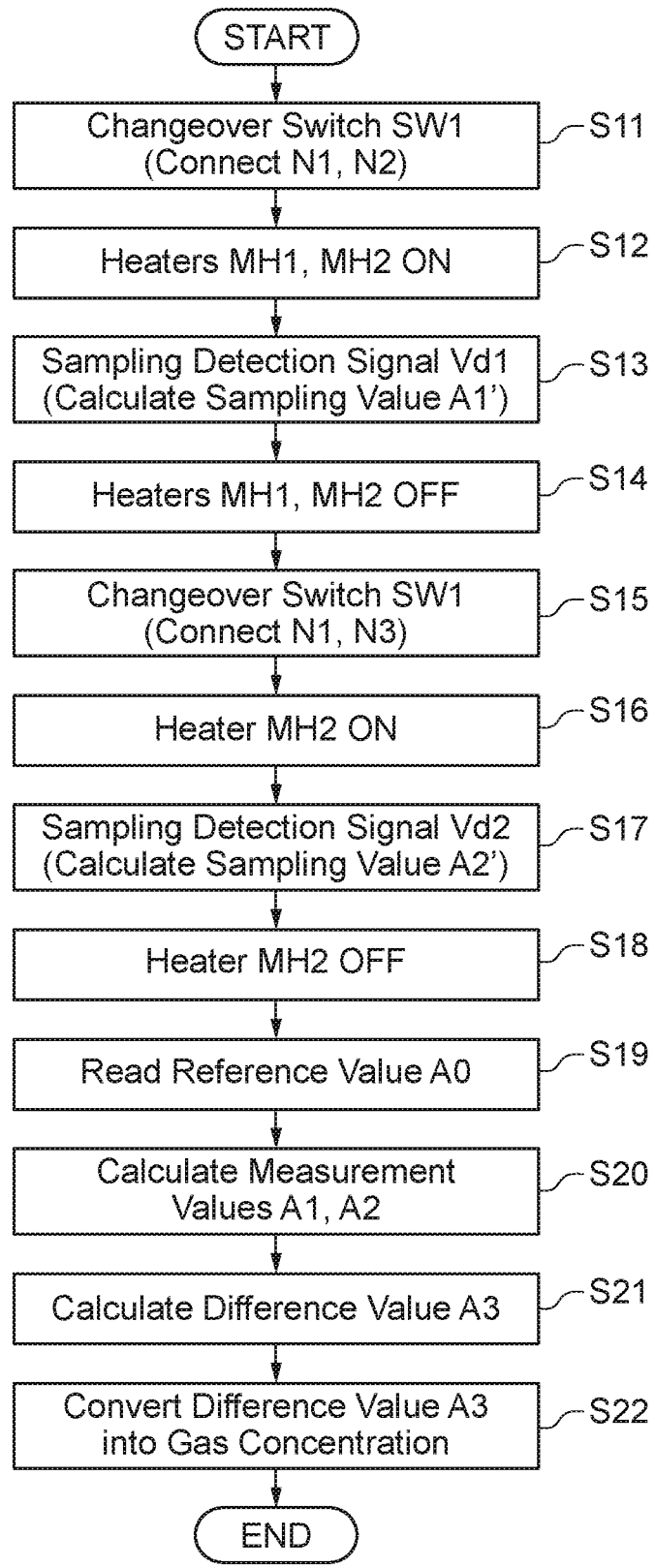
FIG. 4 is as flowchart for explaining the operation of the gas sensor 10A.

FIG. 4 is as flowchart for explaining the operation of the gas sensor 10A according to the present embodiment.

First, the switch SW1 is controlled by the control part 24 included in the signal processing circuit 20 to connect nodes N1 and N2 (step S11). As a result, the first thermistor Rd1 and the second thermistor Rd2 are connected in series, whereby the first sensor part S1 is selected. In this state, control voltages Vmh1 and Vmh2 are set to a Vact level to perform heating using the first and second heater resistors MH1 and MH2 (step S12).

When heating is performed by the first and second heater resistors MH1 and MH2, the first thermistor Rd1 and catalyst CT are heated on the detection part 30 side, while the second thermistor Rd2 and dummy catalyst DCT are heated on the detection part 40 side. Therefore, when combustible gas such as CO gas exists in the measuring environmental atmosphere, combustion is accelerated by the catalyst CT, so that the temperature of the first thermistor Rd1 becomes higher than that of the second thermistor Rd2. The difference in resistance value between the first and second thermistors Rd1 and Rd2 appears as the first detection signal Vd1.

On the other hand, when non-combustible gas (e.g., $CO_2$ gas) having a heat conductivity significantly different from that of air exists in the measuring environmental atmosphere, the heat radiation characteristics of the first and second thermistors Rd1 and Rd2 change and, accordingly, the resistance values thereof also change; however, such a change occurs equally in the first and second thermistors Rd1 and Rd2, so that the first detection signal Vd1 is not influenced. That is, measurement error due to the existence of non-combustible gas having a heat conductivity significantly different from that of air is cancelled. Further, the resistance values of the first and second thermistors Rd1 and Rd2 also change due to aging or a change in environmental temperature; however, such a change also occurs equally in the first and second thermistors Rd1 and Rd2, so that the first detection signal Vd1 is not influenced. Thus, the first detection signal Vd1 output from the first sensor part S1 substantially reflects only the concentration of combustible gas contained in the measuring environmental atmosphere.

The first detection signal Vd1 is converted into the amplification signal Vamp1 by the differential amplifier 21 included in the signal processing circuit 20 and then input to the AD converter 22. The AD converter 22 performs sampling operation at a predetermined timing after the first and second heater resistors MH1 and MH2 start heating, performs digital conversion of the sampled amplification signal Vamp1 to generate a sampling value A1', and supplies the sampling value A1' to the control part 24 (step S13). The sampling operation is preferably started at a timing after a predetermined time period has elapsed from when the first and second heater resistors MH1 and MH2 start heating so as to prevent an overshoot waveform immediately after the start of the heating from being sampled and, more preferably, values sampled for a certain period of time or a plurality of times are averaged. Thereafter, the control voltages Vmh1 and Vmh2 are set back to a ground level to end the heating performed by the first and second heater resistors MH1 and MH2 (step S14).

As described above, the value sampled in step S13 indicates the concentration of combustible gas. However, in addition to CO gas to be detected, a miscellaneous combustible gas which is a non-detection target, such as ethanol, acetic acid, or an organic deodorant, is inevitably detected. That is, the value sampled in step S13 indicates the concentration of the mixture of the detection target gas (CO gas) and the miscellaneous combustible gas which is a non-detection target.

Then, the switch SW1 is controlled by the control part 24 to connect nodes N1 and N3 (step S15). As a result, the second thermistor Rd2 and the resistor R1 are connected in series, whereby the second sensor part S2 is selected. In this state, the control voltage Vmh2 is set to the Vact level to perform heating using the second heater resistor MH2 (step S16). When a series of operations is performed continuously, the control voltage Vmh2 need not be set back to the ground level in step S14 but may be kept at the Vact level (see FIG. 10).

When heating is performed by the second heater resistor MH2, the second thermistor Rd2 and dummy catalyst DCT are heated. Therefore, when miscellaneous gas having a heat conductivity significantly different from that of air, such as ethanol, acetic acid, or an organic deodorant, exists in the measuring environmental atmosphere, the heat radiation characteristics of the second thermistor Rd2 change according to the concentration of the existing miscellaneous gas. A change in the resistance value of the second thermistor Rd2 caused by the change in the heat radiation characteristics thereof appears as the second detection signal Vd2.

On the other hand, CO gas to be detected in the present embodiment is substantially the same in heat conductivity as air (CO gas is closer in heat conductivity to air than miscellaneous gas, including, at least ethanol, acetic acid, or an organic deodorant is), so that the existence of CO gas is hardly reflected on the second detection signal Vd2. Thus, the second detection signal Vd2 output from the second sensor part S2 substantially reflects only the concentration of miscellaneous gas contained in the measuring environmental atmosphere and having a heat conductivity significantly different from that of air.

The second detection signal Vd2 is converted into the amplification signal Vamp2 by the differential amplifier 21 included in the signal processing circuit 20 and then input to the AD converter 22. The AD converter 22 performs sampling operation at a predetermined timing after the second heater resistor MH2 starts heating, performs digital conversion of the sampled amplification signal Vamp2 to generate a measurement value A2', and supplies the measurement value A2' to the control part 24 (step S17). The sampling timing is as described above. Thereafter, the control voltage Vmh2 is set back to the ground level to end the heating performed by the second heater resistor MH2 (step S18).

Then, a reference value A0 stored in the control part 24 is read out (step S19). The reference value corresponds to a sampling value obtained when neither detection target gas nor miscellaneous gas exists in the measuring environmental atmosphere. The reference value A0 may be stored in advance at the time of manufacture or may be obtained through an actual measurement process carried out under conditions where neither detection target gas nor miscellaneous gas exists. When a reference value corresponding to the first sensor part S1 and a reference value corresponding to the second sensor part S2 differ from each other, both of them are read out.

Then, based on the sampling values obtained in steps S13 and S17, measurement values A1 and A2 are calculated (step S20). The measurement value A1 is a value indicating the concentration of gas detected by the first sensor part S1 and is calculated as follows:

$$A1=A1'-A0.$$

On the other hand, the measurement value A2 is a value indicating the concentration of gas detected by the second sensor part S2 and is calculated as follows;

$$A2=A2'-A0.$$

That is, both in the measurement values A1 and A2, a signal component corresponding to the reference value A0 obtained when neither detection target gas nor miscellaneous gas exists in the measuring environmental atmosphere is removed, and only a signal component caused by detected gas is left.

Then, based on the measurement values A1 and A2, a difference value A3 is calculated (step S21). The difference value A3 is calculated as follows:

$$A3=A1-A2.$$

As a result, the gas concentration detected by the second sensor part S2 is canceled from the gas concentration detected by the first sensor part S1. For example, even when a signal component caused by miscellaneous gas such as ethanol, acetic acid, organic deodorant is superimposed on the measurement value A1, the signal component is canceled, and only the signal component caused by CO gas to be detected is left. When there is a difference in detection sensitivity between the first and second sensor parts S1 and S2, sensitivity correction needs to be carried out.

Then, the difference value A3 is converted into a gas concentration, and the series of detection operations are finished (step S22). As described above, according to the gas sensor 10A of the present embodiment, the gas concentration detected by the second sensor part S2 is canceled from the gas concentration detected by the first sensor part S1, so that influence by miscellaneous gas is eliminated. This makes it possible to more accurately detect the concentration of CO gas to be detected.

Figures 5A, 5B, 5C:
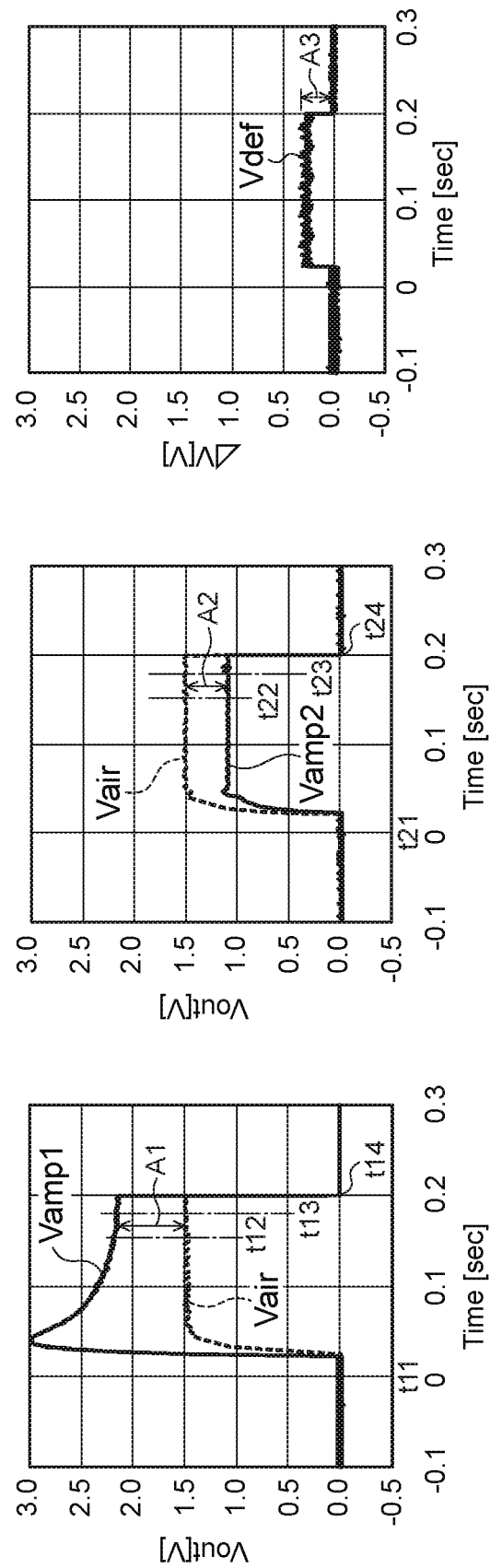
FIGS. 5A to 5C are graphs illustrating an example of the operation of the gas sensor 10A when CO gas and acetic acid coexists in the measuring environmental atmosphere, where

FIGS. 5A to 5C are graphs illustrating an example of the operation of the gas sensor 10A when CO gas and acetic acid coexists in the measuring environmental atmosphere. FIG. 5A illustrates output waveforms of the first sensor part S1, FIG. 5B illustrates output waveforms of the second sensor part S2, and FIG. 5C shows a calculation result of the differential value.

In FIG. 5A, heating by the first and second heater resistors MH1 and MH2 is started at time t11 (step S12) and ended at time t14 (step S14). The heating time is 0.2 sec. As illustrated in FIG. 5A, the amplification signal Vamp1 output from the differential amplifier 21 is overshot immediately after the start of heating. Therefore, sampling is performed during a time period from time t12 to time t13 during which the waveforms are stable (step S13). The waveform Vair illustrated in FIG. 5A is the waveform of a signal output from the differential amplifier 21 when neither detection target gas nor miscellaneous gas exists in the measuring environmental atmosphere in the measurement using the first sensor part S1 and corresponds to the reference value A0 for the first sensor part S1. Thus, the difference (measurement value A1) between the Vamp1 and the Vair indicates a concentration of the mixture of CO gas and acetic acid.

In FIG. 5B, heating by the second heater resistor MH2 is started at time t21 (step S16) and ended at time t24 (step S18). The heating time is 0.2 sec. As illustrated in FIG. 5B, the amplification signal Vamp2 output from the differential amplifier 21 is unstable immediately after the start of heating, so that sampling is performed during a time period from time t22 to time t23 during which the waveforms are stable (step S17). The waveform Vair illustrated in FIG. 5B is the waveform of a signal output from the differential amplifier 21 when neither detection target gas nor miscellaneous gas exists in the measuring environmental atmosphere in the measurement using the second sensor part S2 and corresponds to the reference value A0 for the second sensor part S2. Thus, the difference (measurement value A2) between the Vamp2 and the Vair indicates a concentration of acetic acid.

Then, the measurement value A2 is subtracted from the measurement value A1, and the difference value A3 is obtained. The waveform Vdef illustrated in FIG. 5C is a waveform indicating a signal component corresponding to the difference value A3. Actually, the control part 24 performs calculations using the measurement values A1 and A2 digitized by the AD converter 22, so that the waveform. Vdef illustrated in FIG. 5C is actually not generated.

The waveforms illustrated in FIG. 5B are those after sensitivity correction. For example, assuming that CO detection sensitivity in the first sensor part S1 is 10 μV/ppm, acetic acid detection sensitivity in the first sensor part S1 is 15 μV/ppm, acetic acid detection sensitivity in the second sensor part S2 is 5 μV/ppm, and the gain of the differential amplifier 21 is 100×, there is a three times difference in the acetic acid detection sensitivity between the first and second sensor parts S1 and S2, so the difference needs to be corrected. In FIGS. 5A and 5B, the measurement value A1 is 0.7 V, and the measurement value A2 (after sensitivity correction) is 0.4 V, so that 0.3 V (0.7-0.4) is caused by CO gas. Since the CO detection sensitivity is 10 μV/ppm, and the gain of the differential amplifier 21 is 100×, the concentration of CO gas is calculated as follows:

$$0.3(V)/(10(\mu V/ppm) \times 100)=300 \text{ ppm}.$$

Thus, when there is a difference in miscellaneous gas detection sensitivity between the first and second sensor parts S1 and S2, it is possible to properly cancel the influence of miscellaneous gas by performing sensitivity correction.

As described above, the gas sensor 10A according to the present embodiment can cancel the influence of miscellaneous gas even when CO gas to be detected and the miscellaneous gas coexist and thus can detect the concentration of CO gas to be detected more accurately.

When the detection sensitivity of the first sensor part S1 and that of the second sensor part S2 significantly differ from each other depending on the type of miscellaneous gas, an operation of discriminating the type of the miscellaneous gas is preferably executed in addition to the above operations.

Figure 6:
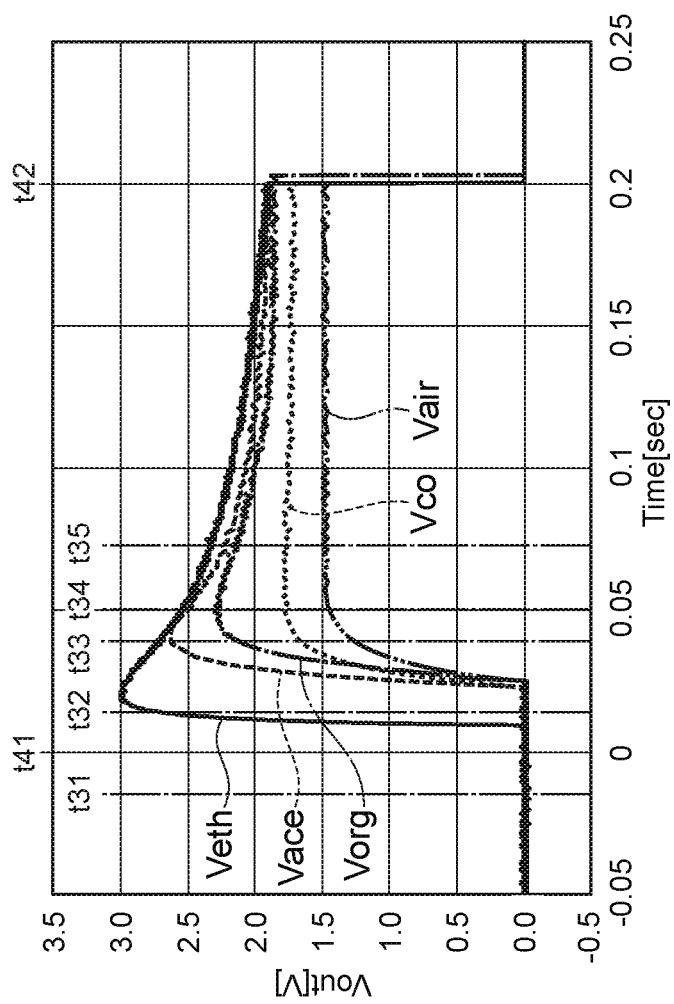
FIG. 6 is a view illustrating the waveforms of signals output from the differential amplifier 21 when various types of gas exist in the measuring environmental atmosphere in the measurement using the first sensor part S1.

FIG. 6 is a view illustrating the waveforms of signals output from the differential amplifier 21 when various types of gas exist in the measuring environmental atmosphere in the measurement using the first sensor part S1.

In FIG. 6, output waveforms of the differential amplifier 21 obtained when heating is performed during a time period from time t41 to time t42 by the first and second heater resistors MH1 and MH2 are illustrated. The waveform Vco illustrated in FIG. 6 is a waveform when gas existing in the atmosphere is CO gas, the waveform Veth is a waveform when gas existing in the atmosphere is ethanol, the waveform Vace is a waveform when gas existing in the atmosphere is acetic acid, the waveform Vorg is a waveform when gas existing in the atmosphere is an organic deodorant, and the waveform Vair is a waveform when only air exists in the atmosphere.

As illustrated in FIG. 6, the waveform of the amplification signal differs depending on the type of gas existing in the atmosphere. In particular, the time between the start of heating and the rising of the waveform or the time until the peak appears, that is, a rising waveform differs depending on the gas type. The table of FIG. 6 shows, for each gas type, the rising start time and the time until the peak appears (rising time). By utilizing the difference in such characteristics, it is possible to discriminate the type of gas existing in the measuring environmental atmosphere.

Figure 7:
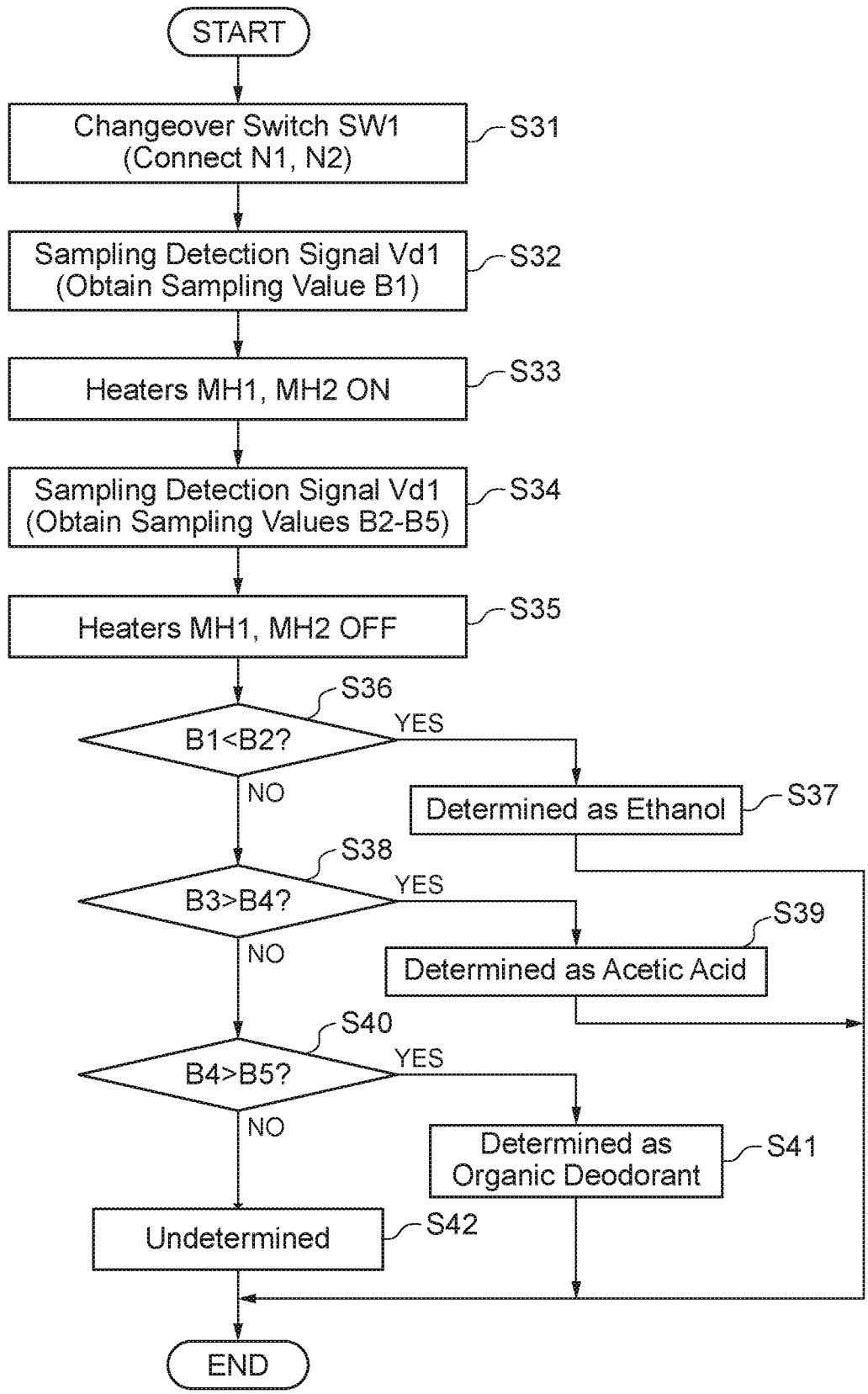
FIG. 7 is a flowchart for explaining the operation of discriminating the type of miscellaneous gas.

FIG. 7 is a flowchart for explaining the operation of discriminating the type of miscellaneous gas.

First, the switch SW1 is controlled by the control part 24 included in the signal processing circuit 20 to connect the nodes N1 and N2 (step S31). As a result, the first thermistor Rd1 and the second thermistor Rd2 are connected in series, whereby the first sensor part S1 is selected. In this state, a sampling value B1 is obtained based on the output of the differential amplifier 21 sampled at time t31 illustrated in FIG. 6 (step S32).

Then, the control voltages Vmh1 and Vmh2 are set to the Vact level at the point of time t41 to perform heating using the first and second heater resistors MH1 and MH2 (step S33). Further, sampling values B2 to B5 are obtained based on the outputs of the differential amplifier 21 sampled at time t32, time t33, time t34, and time t35 illustrated in FIG. 6 (step S34). Thereafter, the control voltages Vmh1 and Vmh2 are set back to the ground level to end the heating performed by the first and second heater resistors MH1 and MH2 (step S35).

After the sampling values B1 to B5 are obtained in this manner, the control part 24 compares the sampling values B1 to B5. Specifically, the control part 24 first compares the sampling values B1 and B2 and determines whether or not the sampling value B2 is larger (step S36). When the sampling value B2 is determined to be larger, gas existing in the measuring environmental atmosphere is determined to be ethanol (step S37). When a negative determination result is obtained in step S37, the control part 24 compares the sampling values B3 and B4 and determines whether or not the sampling value B3 is larger (step S38). When the sampling value B3 is determined to be larger, gas existing in the measuring environmental atmosphere is determined to be acetic acid (step S39). When a negative determination result is obtained in step S39, the control part 24 compares the sampling values B4 and B5 and determines whether or not the sampling value B4 is larger (step S40). When the sampling value B4 is determined to be larger, gas existing in the measuring environmental atmosphere is determined to be an organic deodorant (step S41). When all the above determination results are negative, gas existing in the measuring environmental atmosphere is determined to be neither ethanol, acetic acid, nor organic deodorant (step S42). In this case, it is determined that only air exists in the measuring environmental atmosphere or that CO gas exists in the measuring environmental atmosphere.

The type of miscellaneous gas existing in the atmosphere can be determined according to the above method, thus making it possible to properly correct the difference in detection sensitivity according to the type of miscellaneous gas. As described above, when the miscellaneous gas is acetic acid, there is, e.g., a three times difference in detection sensitivity between the first and second sensor parts S1 and S2. Further, the detection sensitivity difference when the miscellaneous gas is ethanol is e.g., 4.5×, and the detection sensitivity difference when the miscellaneous gas is organic deodorant is e.g., 2×. As described above, even when the detection sensitivity difference between the first and second sensor parts S1 and S2 significantly differ from each other depending on the type of miscellaneous gas, it is possible to apply sensitivity correction in the calculation of the difference value A3 by separately executing the above-described operation of discriminating the type of miscellaneous gas.

FIGS. 8A to 8C are views illustrating the waveforms of signals output from the differential amplifier 21 when various types of gas exist in the measuring environmental atmosphere in the measurement using the first sensor part S1. FIG. 8A illustrates a case where CO gas, ethanol, or a mixture thereof exists, FIG. 8B illustrates a case where CO gas, acetic acid, or a mixture thereof exists, and FIG. 8C illustrates a case where CO gas, organic deodorant, or a mixture thereof exists. FIG. 8D is a table showing, for each type of miscellaneous gas, the ratio of inclination between waveforms obtained when CO gas is present and when not present.

FIGS. 8A to 8C illustrate output waveforms of the differential amplifier 21 obtained when the first and second heater resistors MH1 and MH2 are used to perform a heating operation during a time period from time t61 to time t62. In FIG. 8A, the waveform Vco is a waveform obtained when gas existing in the atmosphere is CO, the waveform Veth is a waveform obtained when gas existing in the atmosphere is ethanol, and the waveform Vmix1 is a waveform obtained when both CO and ethanol exist in the atmosphere. In FIG. 8B, the waveform Vco is a waveform obtained when gas existing in the atmosphere is CO, the waveform. Vace is a waveform obtained when gas existing in the atmosphere is acetic acid, and the waveform Vmix2 is a waveform obtained when both CO and acetic acid exist in the atmosphere. In FIG. 8C, the waveform Vco is a waveform obtained when gas existing in the atmosphere is CO, the waveform Vorg is a waveform obtained when gas existing in the atmosphere is an organic deodorant, and the waveform Vmix3 is a waveform obtained when both CO and organic deodorant exist in the atmosphere.

As illustrated in FIGS. 8A to 8C, the waveform of the amplification signal differs depending on whether or not CO gas is contained together with a predetermined miscellaneous gas. In particular, the difference between the inclination of the waveform immediately after the peak appeared and the inclination of the waveform after a lapse of a predetermined time after the peak differ depending on the presence/absence of CO gas. FIG. 8D shows, for each type of miscellaneous gas, the ratio of inclination between waveforms obtained when CO gas is present and when not present. This table is stored in the control part 24. By utilizing the difference in such characteristics, it is possible to also determine whether or not CO gas is contained together with a predetermined miscellaneous gas.

Figure 9:
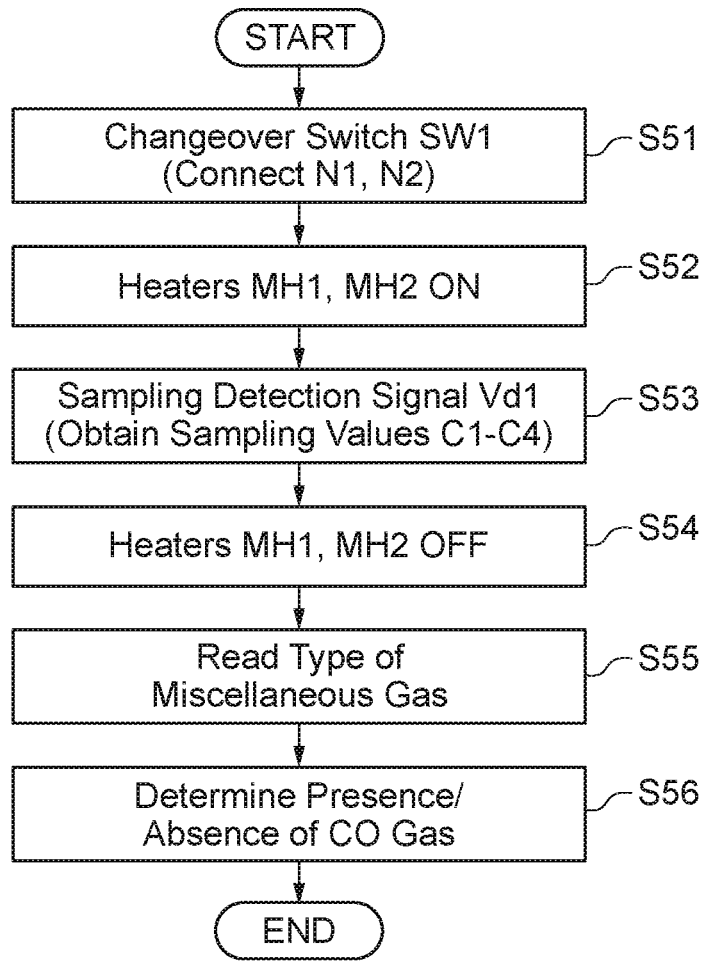
FIG. 9 is a flowchart for explaining an operation of determining the presence/absence of CO gas.

FIG. 9 is a flowchart for explaining an operation of determining the presence/absence of CO gas.

First, the switch SW1 is controlled by the control part 24 included in the signal processing circuit 20 to connect nodes N1 and N2 (step S51). As a result, the first thermistor Rd1 and second thermistor Rd2 are connected in series, whereby the first sensor part S1 is selected. Then, the control voltages Vmh1 and Vmh2 are set to the Vact level at the point of time t61 illustrated in FIG. 8 to perform a heating operation using the first and second heater resistors MH1 and MH2 (step S52). Then, sampling values C1 to C4 are obtained based on the outputs of the differential amplifier 21 sampled at time t51, time t52, t53, and t54 illustrated in FIG. 8 (step S53). Thereafter, the control voltages Vmh1 and Vmh2 are set back to the ground level to end the heating operation performed by the first and second heater resistors MH1 and MH2 (step S54).

Then, the type of miscellaneous gas determined by the method illustrated in the flowchart of FIG. 7 is readout (step S55). Subsequently, the table corresponding to the read miscellaneous gas and sampling values C1 to C4 are referred to, to determine the presence/absence of CO gas (step S56). As shown in the table of FIG. 8D, the ratio between the inclination of a value obtained by (sampling value C1−sampling value C2) and the inclination of a value obtained by (sampling value C3−sampling value C4) depending on the presence/absence of CO gas is already known, so that it is possible to determine whether or not CO gas is contained in the miscellaneous gas by analyzing the sampling values C1 to C4 obtained in step S53.

The thus obtained determination result can be used as reference data. For example, when the CO gas of a concentration exceeding a predetermined value is detected by the method illustrated in the flowchart of FIG. 4 while the CO gas is determined not to be contained by the method illustrated in the flowchart of FIG. 9, it is considered that some sort of abnormality may be occurring or that measurement error may be significantly increasing. In such a case, attention can be drawn by, e.g., generating an error signal.

Figure 10:
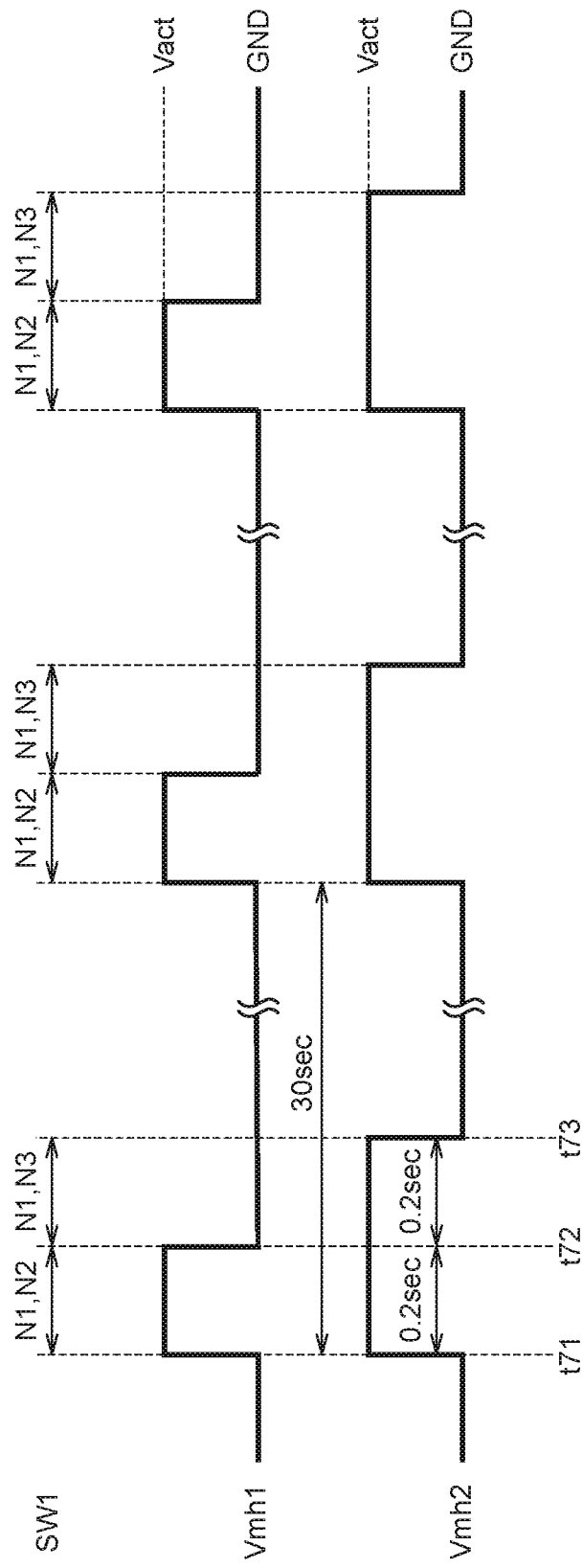
FIG. 10 is a timing chart for explaining the relationship between the switching operation of the switch SW1 and the control voltages Vmh1 and Vmh2.

FIG. 10 is a timing chart for explaining the relationship between the switching operation of the switch SW1 and the control voltages Vmh1 and Vmh2.

In the example illustrated in FIG. 10, the nodes N1 and N2 are connected by the switch SW1 during a time period from time t71 to t72, and the nodes N1 and N3 are connected by the switch SW1 during a time period from time t72 to t73. In conjunction with this, the control voltage Vmh1 is set to the Vact level during a time period from time t71 to t72, and the control voltage Vmh2 is set to the Vact level during a time period from time t71 to t73. As a result, the first and second sensor parts S1 and S2 are alternately activated. For example, the time length between time t71 and time t72 and the time length between time t72 and t73 are both 0.2 sec, and this operation is executed every 30 sec. This allows the concentration of CO gas to be detected every 30 sec. Further, when the concentration of CO gas exceeds a predetermined value, the detection cycle may be reduced to detect the concentration of CO gas more frequently.

Figure 11:
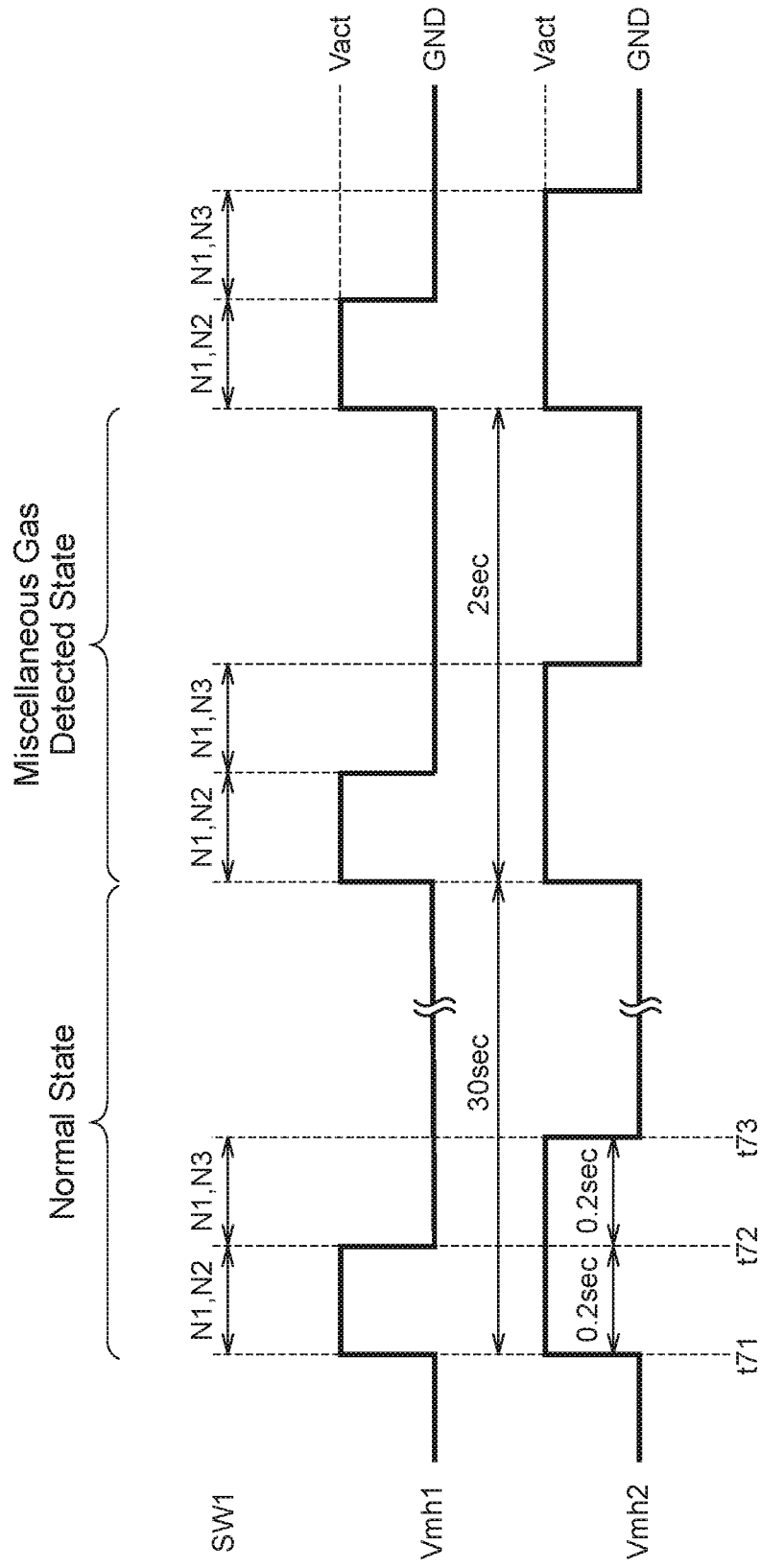
FIG. 11 is another timing chart for explaining the relationship between the switching operation of the switch SW1 and the control voltages Vmh1 and Vmh2.

FIG. 11 is another timing chart for explaining the relationship between the switching operation of the switch SW1 and the control voltages Vmh1 and Vmh2.

In the example illustrated in FIG. 11, in the normal state, that is, when the concentration of miscellaneous gas is less than the detection limit or less than a predetermined value, the detection cycle is set to 30 sec. On the other hand, when miscellaneous gas is detected, or when the concentration of miscellaneous gas is equal to or higher than a predetermined value, the detection cycle is reduced to 2 sec. By reducing the detection cycle when miscellaneous gas is detected, combustion of the miscellaneous gas is accelerated, allowing the miscellaneous gas adhering onto the surface of the catalyst CT to be removed.

Second Embodiment

Figure 12:
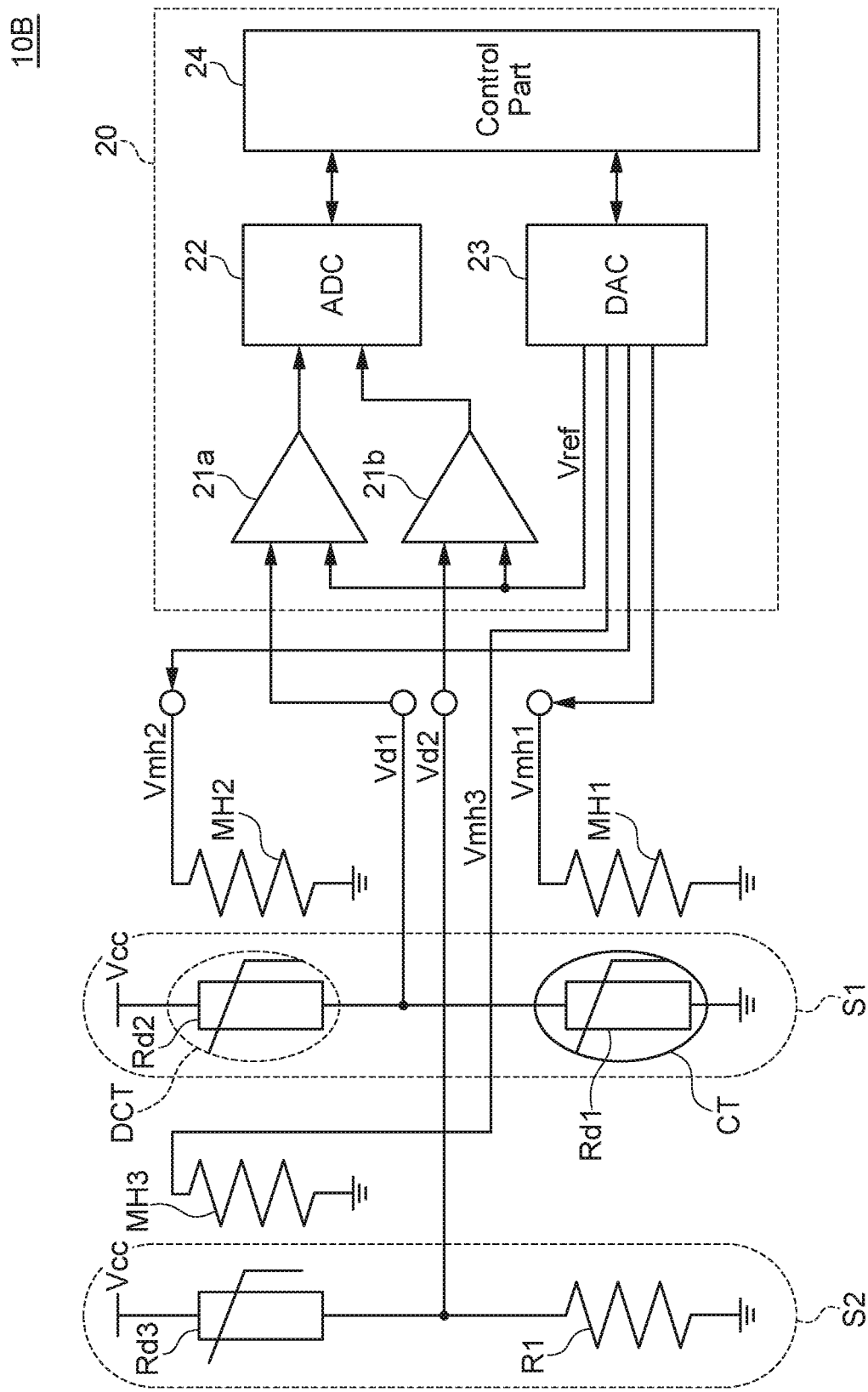
FIG. 12 is a circuit diagram illustrating the configuration of a gas sensor 10B according to a second embodiment of the present invention.

FIG. 12 is a circuit diagram illustrating the configuration of a gas sensor 10B according to the second embodiment of the present invention.

As illustrated in FIG. 12, the gas sensor 10B according to the present embodiment differs from the gas sensor 10A according to the first embodiment in that the first and second sensor parts S1 and S2 are partly not used in common, but are independent of each other.

Specifically, a third thermistor Rd3 and a third heater resistor MH3 for heating the third thermistor Rd3 are additionally provided, and the third thermistor Rd3 and resistor R1 constitute the second sensor part S2. Thus, the second detection signal Vd2 is output from the connection point between the third thermistor Rd3 and the resistor R1. Accordingly, the switch SW1 is removed, and a differential amplifier 21a adapted to receive the first detection signal Vd1 and a differential amplifier 21b adapted to receive the second detection signal Vd2 are provided separately. Other configurations are basically the same as those of the gas sensor 10A according to the first embodiment, so the same reference numerals are given to the same elements, and overlapping description will be omitted.

Figure 13:
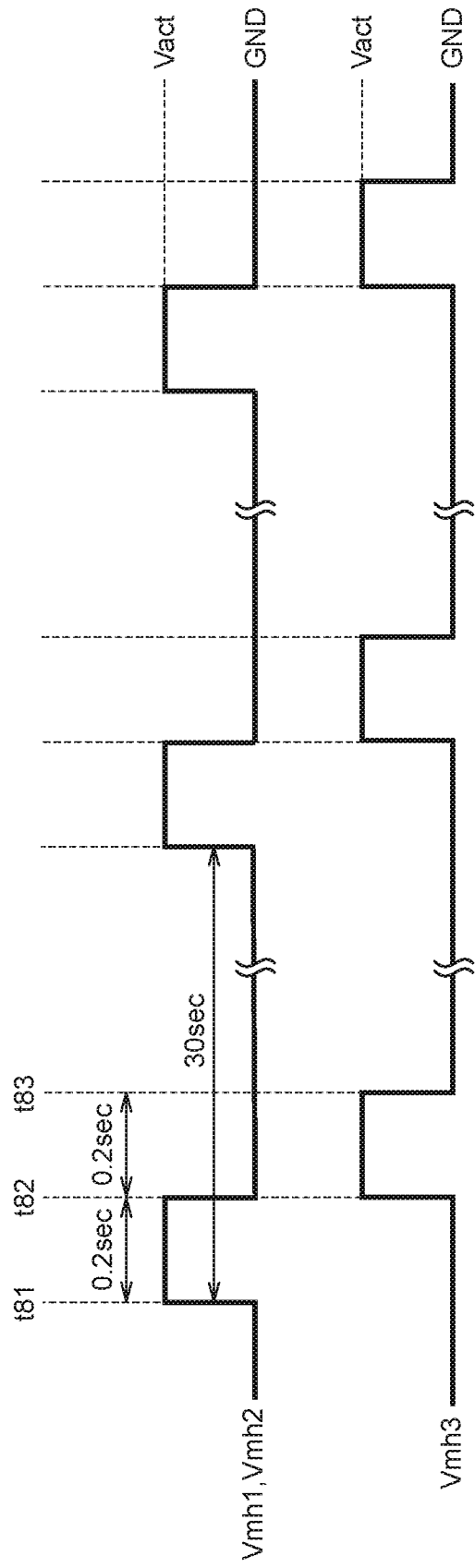
FIG. 13 is a timing chart for explaining changes in the respective control voltages Vmh1 to Vmh3.

FIG. 13 is a timing chart for explaining changes in the respective control voltages Vmh1 to Vmh3.

In the example illustrated in FIG. 13, the control voltages Vmh1 and Vmh2 are set to the Vact level during a time period from time t81 to t82, and the control voltage Vmh3 is set to the Vact level during a time period from time t82 to t83. As a result, the first and second sensor parts S1 and S2 are alternately activated. For example, the time length between time t81 and time t82 and the time length between time t82 and t83 are both 0.2 sec, and this operation is executed every 30 sec. This allows the concentration of CO gas to be detected every 30 sec. Further, when the concentration of CO gas exceeds a predetermined value, the detection cycle may be reduced to detect the concentration of CO gas more frequently.

In the gas sensor 10B according to the present embodiment, the switch SW1 is not provided, and the first and second sensor parts S1 and S2 are independent of each other, so that the activation time period of the first sensor part S1 and that of the second sensor part S2 may be made to overlap each other partially or entirely. Nonetheless, in order to prevent the thermal interference between the first sensor part S1 and the second sensor part S2, their activation time periods should preferably be non-overlapped each other, as illustrated in FIG. 13.

Third Embodiment

Figure 14:
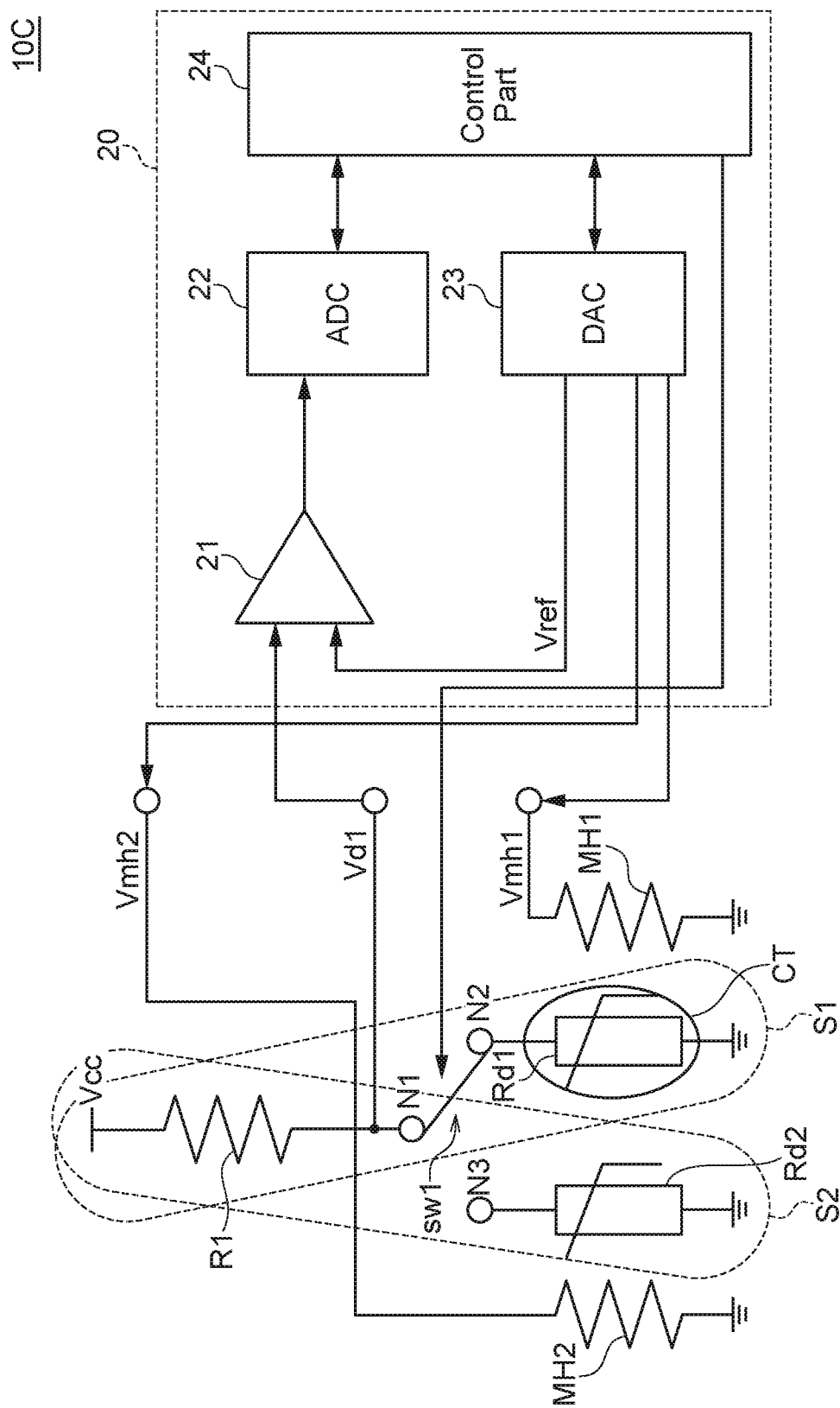
FIG. 14 is a circuit diagram illustrating the configuration of a gas sensor 10C according to a third embodiment of the present invention.

FIG. 14 is a circuit diagram illustrating the configuration of a gas sensor 10C according to the third embodiment of the present invention.

As illustrated in FIG. 14, the gas sensor 10C according to the present embodiment differs from the gas sensor 10A according to the first embodiment in that the second thermistor Rd2 and the resistor R1 are interchanged in position. Accordingly, the dummy catalyst DCT covering the second thermistor Rd2 is omitted. Other configurations are basically the same as those of the gas sensor 10A according to the first embodiment, so the same reference numerals are given to the same elements, and overlapping description will be omitted.

The operation of the gas sensor 10C according to the present embodiment is basically the same as that of the gas sensor 10A according to the first embodiment. However, unlike the gas sensor 10A according to the first embodiment, the first sensor part S1 is constituted by the first thermistor Rd1 and the resistor R1, so that when non-combustible gas (e.g., $CO_2$ gas) having a heat conductivity significantly different from that of air exists in the measuring environmental atmosphere, the heat radiation characteristics of the first thermistor Rd1 change to cause a measurement error.

Such an error can be canceled in the signal processing circuit 20 by detecting the concentration of $CO_2$ gas using the second sensor part S2.

Fourth Embodiment

Figure 15:
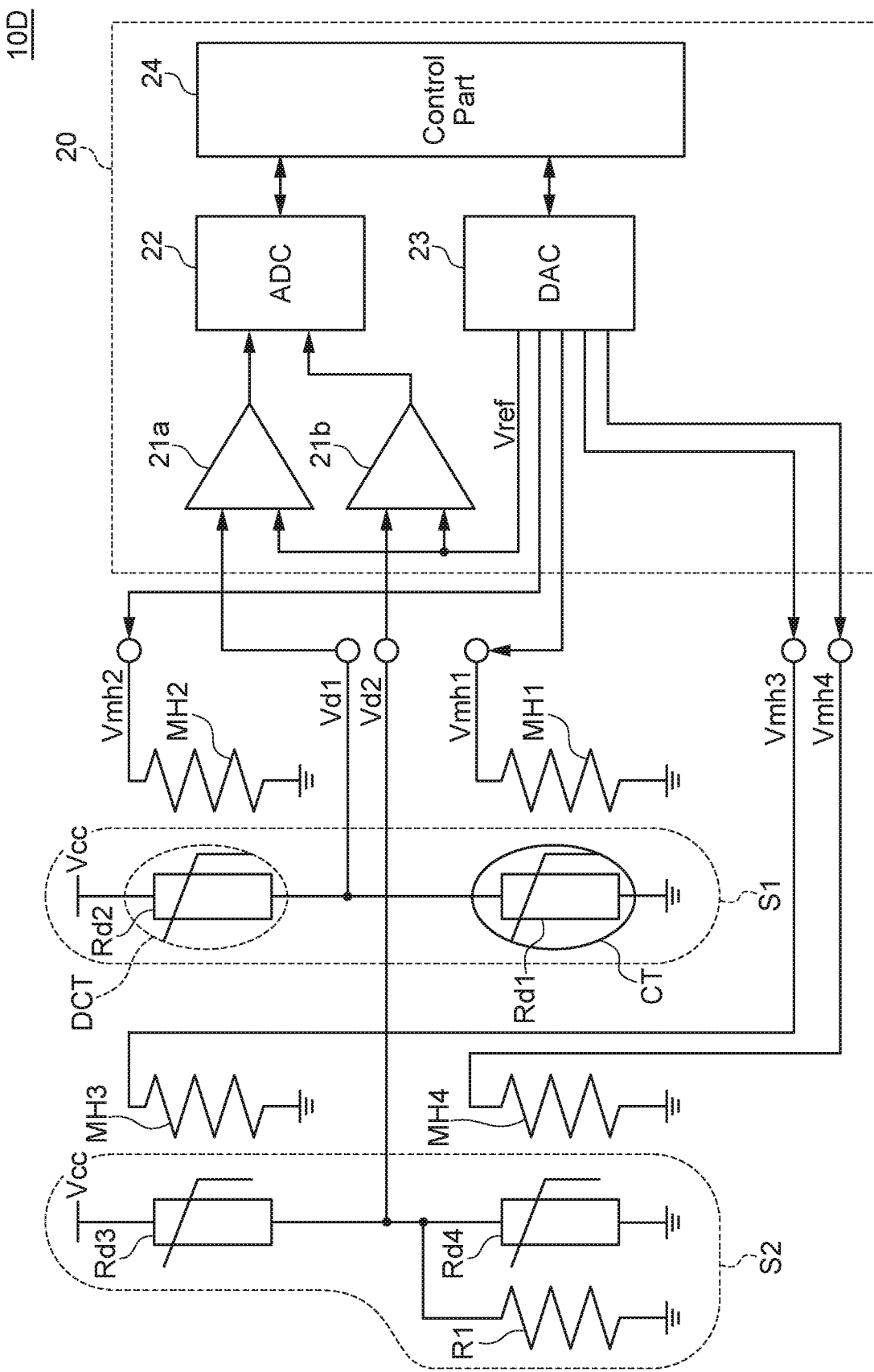
FIG. 15 is a circuit diagram illustrating the configuration of a gas sensor 10D according to a fourth embodiment of the present invention.

FIG. 15 is a circuit diagram illustrating the configuration of a gas sensor 10D according to the fourth embodiment of the present invention.

As illustrated in FIG. 15, the gas sensor 10D according to the present embodiment differs from the gas sensor 10B according to the second embodiment in that a fourth thermistor Rd4 connected in parallel to the resistor R1 of the second sensor part S2 and a fourth heater resistor MH4 for heating the fourth thermistor Rd4 are additionally provided. The fourth heater resistor MH4 is supplied with a control voltage Vmh4 from the DA converter 23. Other configurations are basically the same as those of the gas sensor 10B according to the second embodiment, so the same reference numerals are given to the same elements, and overlapping description will be omitted.

In the present embodiment, the third and fourth thermistors Rd3 and Rd4 are heated to mutually different temperatures. This can be realized by setting the control voltages Vmh3 and Vmh4 to mutually different levels. When miscellaneous gas exists in the measuring environmental atmosphere in a state where the third and fourth thermistors Rd3 and Rd4 are heated, the heat radiation characteristics of the third and fourth thermistors Rd3 and Rd4 change according to the concentration of miscellaneous gas. Since the third and fourth thermistors Rd3 and Rd4 are heated to mutually different temperatures, the detection sensitivity with respect to the miscellaneous gas in the third thermistor Rd3 and the detection sensitivity with respect to the miscellaneous gas in the fourth thermistor Rd4 differ from each other.

Further, the heat radiation characteristics of the third and fourth thermistors Rd3 and Rd4 change also according to the humidity ($H_2O$) in the measuring environmental atmosphere. Since the third and fourth thermistors Rd3 and Rd4 are heated to mutually different temperatures, the detection sensitivity with respect to the humidity in the third thermistor Rd3 and the detection sensitivity with respect to the humidity in the fourth thermistor Rd4 differ from each other.

Figure 16:
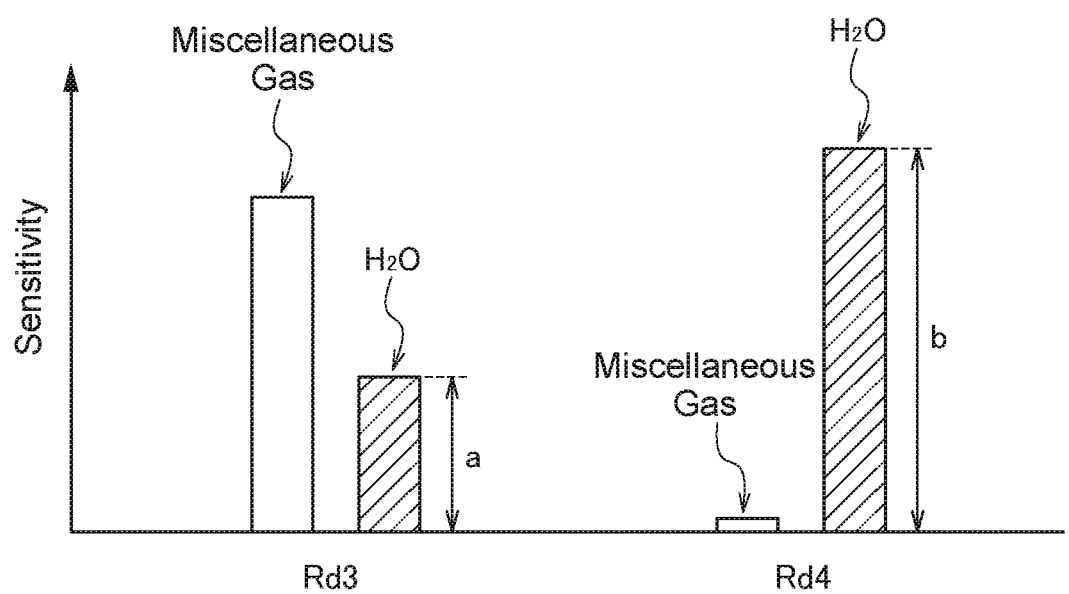
FIG. 16 is a schematic graph for explaining the detection sensitivities of the third and fourth thermistors Rd3 and Rd4.

FIG. 16 is a schematic graph for explaining the detection sensitivities of the third and fourth thermistors Rd3 and Rd4.

As illustrated in FIG. 16, the detection sensitivity with respect to the miscellaneous gas in the third thermistor Rd3 is high to some extent, while the detection sensitivity with respect to the miscellaneous gas in the fourth thermistor Rd4 is very low and ignorable. On the other hand, the detection sensitivity with respect to the humidity in the third thermistor Rd3 is a, while the detection sensitivity with respect to the humidity in the fourth thermistor Rd4 is b ($\neq$a). Therefore, the influence of the humidity may unfavorably be reflected on the second detection signal Vd2 in a configuration in which the third and fourth thermistors Rd3 and Rd4 are simply connected in series.

Thus, in the gas sensor 10D according to the present embodiment, the resistance value of the resistor R1 connected in parallel to the fourth thermistor Rd4 is set to a predetermined value so as to cancel a change in the second detection signal Vd2 according to the humidity. As described above, assuming that the detection sensitivity with respect to the humidity in the third thermistor Rd3 is a, the detection sensitivity with respect to the humidity in the fourth thermistor Rd4 is b, and the resistance value of the fourth thermistor Rd4 is Rd4, the resistance value of the resistor R1 is set to R1=(b/a)×Rd4, whereby it is possible to substantially cancel a change in the second detection signal Vd2 according to the humidity.

As a result, the influence that the humidity has on the third thermistor Rd3 and the influence that the humidity has on the fourth thermistor Rd4 are effectively equal to each other, preventing the second detection signal Vd2 from changing even with a change in the humidity. Thus, the level of the second detection signal Vd2 is determined by the concentration of miscellaneous gas.

Figure 17:
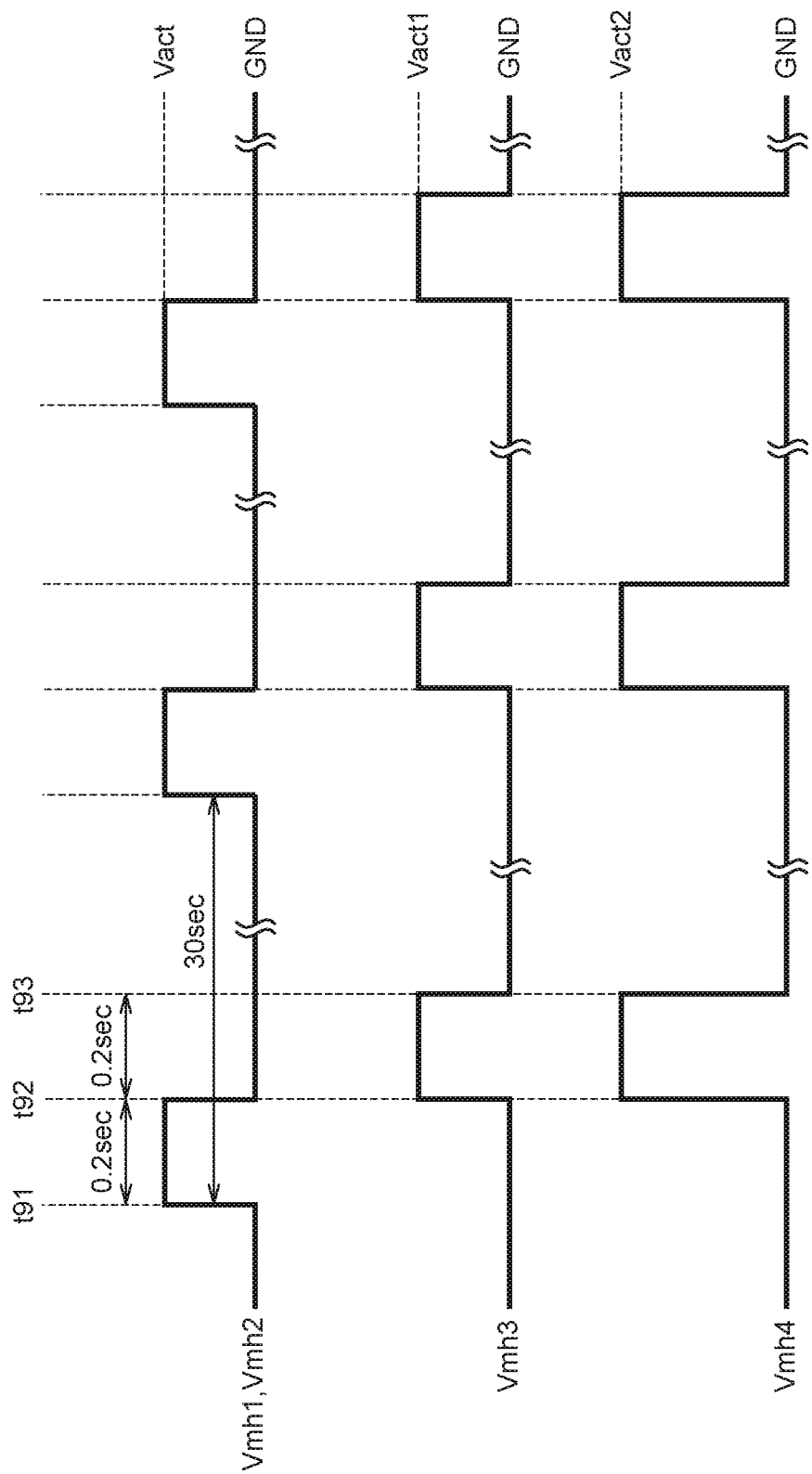
FIG. 17 is a timing chart illustrating an example of the waveforms of the respective control voltages Vmh1 to Vmh4.

FIG. 17 is a timing chart illustrating an example of the waveforms of the respective control voltages Vmh1 to Vmh4.

In the example illustrated in FIG. 17, the control voltages Vmh1 and Vmh2 are set to the Vact level during a time period from time t91 to t92, and the control voltages Vmh3 and Vmh4 are set respectively to a Vact1 level and a Vact2 level during a time period from time t92 to t93. As a result, the first and second sensor parts S1 and S2 are alternately activated. For example, the time length between time t91 and time t92 and the time length between time t92 and t93 are both 0.2 sec, and this operation is executed every 30 sec. This allows the concentration of CO gas to be detected every 30 sec. Further, when the concentration of CO gas exceeds a predetermined value, the detection cycle may be reduced to detect the concentration of CO gas more frequently.

In the gas sensor 10D according to the present embodiment, the first and second sensor parts S1 and S2 are independent of each other, so that $CO_2$ gas can also be detected using the second sensor part S2. To detect $CO_2$ gas using the second sensor part S2, the third and fourth thermistors Rd3 and Rd4 are heated to 150° C. and 300° C., respectively. That is, when the heating temperature is equal to or lower than 150° C., a sufficiently high sensitivity with respect to the concentration of $CO_2$ gas can be obtained, while when the heating temperature exceeds 150° C., the sensitivity with respect to the concentration of $CO_2$ gas is lowered, and when the heating temperature reaches 300° C., the sensitivity with respect to the concentration of $CO_2$ gas becomes substantially zero. Actually, even when the heating temperature is 300° C., slight sensitivity with respect to $CO_2$ gas exists; however, the sensitivity in this case is significantly lower (about 1/10 or lower) than that when the heating temperature is 150° C. and can thus be substantially ignorable.

Further, the sensitivity a with respect to the humidity when the heating temperature of the third thermistor Rd3 differs from the sensitivity b with respect to the humidity when the heating temperature of the fourth thermistor Rd4. Specifically, the sensitivity a is about 120 μV/% RH, and the sensitivity b is about 200 μV/% RH. Accordingly, in this case, the resistance value of the resistor R1 is set to R1=(200/120)×Rd4=(5/3)×Rd4.

As a result, the influence that the humidity has on the third thermistor Rd3 and the influence that the humidity has on the fourth thermistor Rd4 are effectively equal to each other, thus preventing the second detection signal Vd2 from changing even with a change in the humidity. Accordingly, the level of the second detection signal Vd2 is determined by the concentration of $CO_2$ gas. As described above, the gas sensor 10D according to the present embodiment can detect not only the concentration of combustible gas such as CO gas, but also the concentration of $CO_2$ gas.

Further, in the present embodiment, the third and fourth thermistors Rd3 and Rd4 constitute a bridge circuit, so that like the first sensor part S1, deterioration in the thermistor due to aging is suppressed also in the second sensor part S2, allowing reduction in measurement error.

While the preferred embodiment of the present invention has been described, the present invention is not limited to the above embodiment and may be practiced in various forms without departing from the sprit and scope of the present invention.

For example, in the present invention, the measuring environmental atmosphere need not be air and may be some other type of gas different from air.

REFERENCE SIGNS LIST 10A-10C gas sensor
20 signal processing circuit
21, 21a, 21b differential amplifier
22 AD converter
23 DA converter
24 control part
30, 40 detection part
31, 41 substrate
32, 33, 42, 43 insulating film
34, 44 heater protective film
35, 45 thermistor electrode
36, 46 thermistor protective film
37a-37d, 47a-47d electrode pad
51 ceramic package
52 lid
43 vent hole
54 package electrode
55 bonding wire
56 external terminal
CT catalyst
DCT dummy catalyst
MH1-MH4 heater resistor
N1-N3 node
R1 resistor
Rd1-Rd4 thermistor
S1 first sensor part
S2 second sensor part
SW1 switch

What is claimed is:

1. A gas sensor comprising:
    a first sensor part that can detect a concentration of a mixture of a first gas and a second gas;
    a second sensor part having higher detection sensitivity with respect to the second gas than with respect to the first gas; and
    a signal processing circuit that subtracts a concentration of the second gas detected by the second sensor part from a mixture concentration detected by the first sensor part to derive a concentration of the first gas,
    wherein the first and second gases are combustible gas,
    wherein the first sensor part is a contact combustion type sensor,
    wherein the first gas is closer in heat conductivity to a measuring environmental atmosphere than the second gas is,
    wherein the second sensor part is a heat conduction type sensor,
    wherein the first sensor part includes a first thermistor and a catalyst disposed near the first thermistor,
    wherein the second sensor part includes a second thermistor and does not include a catalyst near the second thermistor,
    wherein the second sensor part further includes a resistor,
    wherein the second thermistor is shared between the first and second sensor parts,
    wherein the first sensor part outputs a first detection signal from a connection point between the first and second thermistors, and
    wherein the second sensor part outputs a second detection signal from a connection point between the second thermistor and the resistor.

2. The gas sensor as claimed in claim 1,
    wherein the first gas is CO gas, and
    wherein the second gas is ethanol, acetic acid, or an organic deodorant.

3. The gas sensor as claimed in claim 1, wherein the second sensor part further includes a dummy catalyst disposed near the second thermistor and having no catalytic function.

4. The gas sensor as claimed in claim 1, wherein the signal processing circuit determines a type of the second gas based on the first detection signal.

5. The gas sensor as claimed in claim 4, wherein the signal processing circuit determines the type of the second gas from a rising waveform of the first detection signal.

6. The gas sensor as claimed in claim 1, wherein the signal processing circuit determines a presence/absence of the first gas according to an inclination of the first detection signal.

7. The gas sensor as claimed in claim 1,
    wherein the signal processing circuit calculates the concentration of the first gas in a predetermined detection cycle, and
    wherein a detection cycle is reduced when the concentration of the second gas detected by the second sensor part exceeds a predetermined value.

8. The gas sensor as claimed in claim 1, wherein the signal processing circuit corrects a difference between detection sensitivity with respect to the second gas by the first sensor part and detection sensitivity with respect to the second gas by the second sensor part.

9. A gas sensor comprising:
    a first sensor part that can detect a concentration of a mixture of a first gas and a second gas;
    a second sensor part having higher detection sensitivity with respect to the second gas than with respect to the first gas; and
    a signal processing circuit that subtracts a concentration of the second gas detected by the second sensor part from a mixture concentration detected by the first sensor part to derive a concentration of the first gas,
    wherein the first and second gases are combustible gas,
    wherein the first sensor part is a contact combustion type sensor,
    wherein the first gas is closer in heat conductivity to a measuring environmental atmosphere than the second gas is,
    wherein the second sensor part is a heat conduction type sensor,
    wherein the first sensor part includes first and second thermistors and a catalyst disposed near the first thermistor,
    wherein the second sensor part includes a third thermistor and a resistor,
    wherein the first sensor part outputs a first detection signal from a connection point between the first and second thermistors,
    wherein the second sensor part outputs a second detection signal from a connection point between the third thermistor and the resistor, and wherein a catalyst is not disposed near the second thermistor.

10. The gas sensor as claimed in claim 9, wherein the first sensor part further includes a dummy catalyst disposed near the second thermistor and having no catalytic function.

11. The gas sensor as claimed in claim 10, wherein the second sensor part further includes a fourth thermistor connected in parallel to the resistor.

12. The gas sensor as claimed in claim 9, wherein the second sensor part further includes a fourth thermistor connected in parallel to the resistor.

* * * * *